(12) United States Patent
Smith et al.

(10) Patent No.: US 8,101,773 B2
(45) Date of Patent: *Jan. 24, 2012

(54) HYDROXY METHYL PHENYL PYRAZOLYL UREA COMPOUNDS USEFUL IN THE TREATMENT OF CANCER

(75) Inventors: Roger Smith, Chester Springs, PA (US); Dhanapalan Nagarathnam, Bethany, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/520,609

(22) PCT Filed: Dec. 20, 2007

(86) PCT No.: PCT/US2007/088365
§ 371 (c)(1),
(2), (4) Date: Nov. 2, 2009

(87) PCT Pub. No.: WO2008/079968
PCT Pub. Date: Jul. 3, 2008

(65) Prior Publication Data
US 2010/0063107 A1    Mar. 11, 2010

Related U.S. Application Data

(60) Provisional application No. 60/875,830, filed on Dec. 20, 2006, provisional application No. 60/986,773, filed on Nov. 9, 2007.

(51) Int. Cl.
*A61K 31/44* (2006.01)
*C07D 401/00* (2006.01)

(52) U.S. Cl. .................................. 546/275.4; 514/341

(58) Field of Classification Search .................. None
See application file for complete search history.

(56) References Cited

U.S. PATENT DOCUMENTS
7,838,524 B2 * 11/2010 Lee et al. ............... 514/235.8

FOREIGN PATENT DOCUMENTS
| WO | WO 2005/110994 A | 11/2005 |
| WO | WO 2006/105844 A | 10/2006 |
| WO | WO 2007/064872 A | 6/2007 |

OTHER PUBLICATIONS

Vippagunta, S. et al Adv. Drug Deliv. Rev., vol. 48, 2001, pp. 3-26.*
Tavora de Albuquerque Silva, A. et al Mini-Revs. in Med. Chem., vol. 5, 2005, pp. 893-914.*
"International Search Report," International Application No. PCT/US2007/088365, Date of completion of International Search Report Apr. 10, 2008, Date of mailing international search report May 9, 2008, European Patent Office (place of mailing).

* cited by examiner

*Primary Examiner* — Janet Andres
*Assistant Examiner* — Heidi Reese
(74) *Attorney, Agent, or Firm* — Millen, White, Zelano & Branigan, P.C.

(57) ABSTRACT

The compound 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide and alternative forms thereof (e.g., salts, solvates, hydrates, prodrugs, polymorphs and metabolites); pharmaceutical compositions which contain them; and methods for treating cancer using them.

16 Claims, No Drawings

HYDROXY METHYL PHENYL PYRAZOLYL UREA COMPOUNDS USEFUL IN THE TREATMENT OF CANCER

This application is a National Stage Entry of PCT/US2007/088365, filed Dec. 20, 2007, which claims the benefit of U.S. Provisional Patent Application No(s). 60/875,830, filed Dec. 20, 2006 and 60/986,773, filed Nov. 9, 2007.

FIELD OF THE INVENTION

This invention relates to novel hydroxy methyl phenyl pyrazolyl urea compounds, pharmaceutical compositions containing such compounds and the use of these compounds or compositions for treating hyper-proliferative and/or angiogenesis disorders, as a sole agent or in combination with other active ingredients, e.g., cytotoxic therapies.

BACKGROUND OF THE INVENTION

To support progressive tumor growth beyond the size of 1-2 mm$^3$, it is recognized that tumor cells require a functional stroma, a support structure consisting of fibroblast, smooth muscle cells, endothelial cells, extracellular matrix proteins, and soluble factors (Folkman, J., Semin Oncol, 2002, 29 (6 Suppl 16), 15-8). Tumors induce the formation of stromal tissues through the secretion of soluble growth factors such as PDGF and transforming growth factor-beta (TGF-beta), which in turn stimulate the secretion of complimentary factors by host cells such as fibroblast growth factor (FGF), epidermal growth factor (EGF), and vascular endothelial growth factor (VEGF). These stimulatory factors induce the formation of new blood vessels, or angiogenesis, which brings oxygen and nutrients to the tumor and allows it to grow and provides a route for metastasis. It is believed some therapies directed at inhibiting stroma formation will inhibit the growth of epithelial tumors from a wide variety of histological types. (George, D. Semin Oncol, 2001, 28 (5 Suppl 17), 27-33; Shaheen, R. M., et al., Cancer Res, 2001, 61 (4), 1464-8; Shaheen, R. M., et al. Cancer Res, 1999, 59 (21), 5412-6). However, because of the complex nature and the multiple growth factors involved in angiogenesis process and tumor progression, an agent targeting a single pathway may have limited efficacy. It is desirable to provide treatment against a number of key signaling pathways utilized by tumors to induce angiogenesis in the host stroma. These include, for example, PDGF, a potent stimulator of stroma formation (Ostman, A. and C. H. Heldin, Adv Cancer Res, 2001, 80, 1-38), FGF, a chemo-attractant and mitogen for fibroblasts and endothelial cells, and VEGF, a potent regulator of vascularization. HGF (hepatocyte growth factor) represents an additional signalling growth factor of interest.

PDGF is a key regulator of stromal formation, which is secreted by many tumors in a paracrine fashion and is believed to promote the growth of fibroblasts, smooth muscle and endothelial cells, promoting stroma formation and angiogenesis. PDGF was originally identified as the v-sis oncogene product of the simian sarcoma virus (Heldin, C. H., et al., J Cell Sci Suppl, 1985, 3, 65-76). The growth factor is made up of two peptide chains, referred to as A or B chains which share 60% homology in their primary amino acid sequence. The chains are disulfide cross linked to form the 30 kDa mature protein composed of either AA, BB or AB homo- or heterodimmers. PDGF is found at high levels in platelets, and is expressed by endothelial cells and vascular smooth muscle cells. In addition, the production of PDGF is up regulated under low oxygen conditions such as those found in poorly vascularized tumor tissue (Kourembanas, S., et al., Kidney Int, 1997, 51 (2), 438-43). PDGF binds with high affinity to the PDGF receptor, (PDGFR) a 1106 amino acid 124 kDa transmembrane tyrosine kinase receptor (Heldin, C. H., A. Ostman, and L. Ronnstrand, Biochim Biophys Acta, 1998, 1378 (1), 79-113). PDGFR is found as homo- or heterodimer chains which have 30% homology overall in their amino acid sequence and 64% homology between their kinase domains (Heldin, C. H., et al. Embo J, 1988, 7 (5), 1387-93). PDGFR is a member of a family of tyrosine kinase receptors with split kinase domains that includes VEGFR2 (KDR), VEGFR3 (Flt4), c-Kit, and FLT3. The PDGF receptor is expressed primarily on fibroblast, smooth muscle cells, and pericytes and to a lesser extent on neurons, kidney mesangial, Leydig, and Schwann cells of the central nervous system. Upon binding to the receptor, PDGF induces receptor dimerization and undergoes auto- and trans-phosphorylation of tyrosine residues which increase the receptors' kinase activity and promotes the recruitment of downstream effectors through the activation of SH2 protein binding domains. A number of signaling molecules form complexes with activated PDGFR including PI-3-kinase, phospholipase C-gamma, src and GAP (GTPase activating protein for p21-ras) (Soskic, V., et al. Biochemistry, 1999, 38 (6), 1757-64). Through the activation of PI-3-kinase, PDGF activates the Rho signaling pathway inducing cell motility and migration, and through the activation of GAP, induces mitogenesis through the activation of p21-ras and the MAPK signaling pathway.

In adults, it is believed the major function of PDGF is to facilitate and increase the rate of wound healing and to maintain blood vessel homeostasis (Baker, E. A. and D. J. Leaper, Wound Repair Regen, 2000, 8 (5), 392-8; Yu, J., A. Moon, and H. R. Kim, Biochem Biophys Res Commun, 2001, 282 (3), 697-700). In addition to its role in wound healing PDGF is known to help maintain vascular homeostasis. During the development of new blood vessels, PDGF recruits pericytes and smooth muscle cells that are needed for the structural integrity of the vessels. PDGF is thought to play a similar role during tumor neovascularization. As part of its role in angiogenesis PDGF controls interstitial fluid pressure, regulating the permeability of vessels through its regulation of the interaction between connective tissue cells and the extracellular matrix. Inhibiting PDGFR activity can lower interstitial pressure and facilitate the influx of cytotoxics into tumors improving the anti-tumor efficacy of these agents (Pietras, K., et al. Cancer Res, 2002, 62 (19), 5476-84; Pietras, K., et al. Cancer Res, 2001, 61 (7), 2929-34).

PDGF can promote tumor growth through either the paracrine or autocrine stimulation of PDGFR receptors on stromal cells or tumor cells directly, or through the amplification of the receptor or activation of the receptor by recombination. Over expressed PDGF can transform human melanoma cells and keratinocytes (Forsberg, K., et al. Proc Natl Acad Sci USA., 1993. 90 (2), 393-7; Skobe, M. and N. E. Fusenig, Proc Natl Acad Sci USA, 1998. 95 (3), 1050-5), two cell types that do not express PDGF receptors, presumably by the direct effect of PDGF on stroma formation and induction of angiogenesis. This paracrine stimulation of tumor stroma is also observed in carcinomas of the colon, lung, breast, and prostate (Bhardwaj, B., et al. Clin Cancer Res, 1996, 2 (4), 773-82; Nakanishi, K., et al. Mod Pathol, 1997, 10 (4), 341-7; Sundberg, C., et al. Am J Pathol, 1997, 151 (2), 479-92; Lindmark, G., et al. Lab Invest, 1993, 69 (6), 682-9; Vignaud, J. M., et al, Cancer Res, 1994, 54 (20), 5455-63) where the tumors express PDGF, but not the receptor. The autocrine stimulation of tumor cell growth, where a large faction of tumors analyzed express both the ligand PDGF and the receptor, has been reported in glioblastomas (Fleming, T. P., et al. Cancer Res, 1992, 52 (16), 4550-3), soft tissue sarcomas (Wang, J., M. D. Coltrera, and A. M. Gown, Cancer Res, 1994, 54 (2), 560-4) and cancers of the ovary (Henriksen, R., et al. Cancer Res, 1993, 53 (19), 4550-4), prostate (Fudge, K., C. Y. Wang, and M. E. Stearns, Mod Pathol, 1994, 7 (5), 549-54), pancreas (Funa, K., et al. Cancer Res, 1990, 50 (3), 748-53) and lung (Antoniades, H. N., et al., Proc Natl Acad Sci USA, 1992, 89 (9), 3942-6). Ligand independent activation of the receptor is found to a lesser extent but has been reported in chronic myelomonocytic leukemia (CMML) where the chromosomal translocation event forms a fusion protein between the Ets-like transcription factor TEL and the PDGF receptor. In addition, activating mutations in PDGFR have been found in gastrointestinal stromal tumors in which c-Kit activation is not involved (Heinrich, M. C., et al., Science, 2003, 9, 9).

Certain PDGFR inhibitors will interfere with tumor stromal development and are believed to inhibit tumor growth and metastasis.

Another major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are reported to be highly specific for vascular endothelial cells (for reviews, see: Farrara et al. Endocr. Rev. 1992, 13, 18; Neufield et al. FASEB J. 1999, 13, 9).

VEGF expression is reported to be induced by hypoxia (Shweiki et al. Nature 1992, 359, 843), as well as by a variety of cytokines and growth factors, such as interleukin-1, interleukin-6, epidermal growth factor and transforming growth factor. To date, VEGF and the VEGF family members have been reported to bind to one or more of three transmembrane receptor tyrosine kinases (Mustonen et al. *J. Cell Biol.*, 1995, 129, 895), VEGF receptor-1 (also known as flt-1 (fms-like tyrosine kinase-1)), VEGFR-2 (also known as kinase insert domain containing receptor (KDR); the murine analogue of KDR is known as fetal liver kinase-1 (flk-1)), and VEGFR-3 (also known as flt-4). KDR and flt-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependent tyrosine phosphorylation in intact cells, whereas flt-1 displays a weak response. Thus, binding to KDR is believed to be a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. It is believed regulation of the VEGF-mediated signal transduction cascade by some agents can provide a useful mode for control of abnormal angiogenesis and/or hyperpermeability processes.

The vascular endothelial growth factors (VEGF, VEGF-C, VEGF-D) and their receptors (VEGFR2, VEGFR3) are not only key regulators of tumor angiogenesis, but also lymphangiogenesis. VEGF, VEGF-C and VEGF-D are expressed in most tumors, primarily during periods of tumor growth and, often at substantially increased levels. VEGF expression is stimulated by hypoxia, cytokines, oncogenes such as ras, or by inactivation of tumor suppressor genes (McMahon, G. *Oncologist* 2000, 5 (Suppl. 1), 3-10; McDonald, N. Q.; Hendrickson, W. A. *Cell* 1993, 73, 421-424)

The biological activities of the VEGFs are mediated through binding to their receptors. It is believed VEGFR3 (also called Flt-4) is predominantly expressed on lymphatic endothelium in normal adult tissues and that VEGFR3 function is needed for new lymphatic vessel formation, but not for maintenance of the pre-existing lymphatics. VEGFR3 is also upregulated on blood vessel endothelium in tumors.

Recently VEGF-C and VEGF-D, ligands for VEGFR3, have been identified as regulators of lymphangiogenesis in mammals. Lymphangiogenesis induced by tumor-associated lymphangiogenic factors could promote the growth of new vessels into the tumor, providing tumor cells access to systemic circulation. Cells that invade the lymphatics could find their way into the bloodstream via the thoracic duct. Tumor expression studies have allowed a direct comparison of VEGF-C, VEGF-D and VEGFR3 expression with clinicopathological factors that relate directly to the ability of primary tumors to spread (e.g., lymph node involvement, lymphatic invasion, secondary metastases, and disease-free survival). In many instances, these studies demonstrate a statistical correlation between the expression of lymphangiogenic factors and the ability of a primary solid tumor to metastasize (Skobe, M. et al. *Nature Med.* 2001, 7 (2), 192-198; Stacker, S. A. et al. *Nature Med.* 2001, 7 (2), 186-191; Makinen, T. et al. *Nature Med.* 2001, 7 (2), 199-205; Mandriota, S. J. et al. *EMBO J.* 2001, 20 (4), 672-82; Karpanen, T. et al. *Cancer Res.* 2001, 61 (5), 1786-90; Kubo, H. et al. *Blood* 2000, 96 (2), 546-53).

Hypoxia appears to be an important stimulus for VEGF production in malignant cells. Activation of p38 MAP kinase is required for VEGF induction by tumor cells in response to hypoxia (Blaschke, F. et al. *Biochem. Biophys. Res. Commun.* 2002, 296, 890-896; Shemirani, B. et al. *Oral Oncology* 2002, 38, 251-257). In addition to its involvement in angiogenesis through regulation of VEGF secretion, p38 MAP kinase promotes malignant cell invasion, and migration of different tumor types through regulation of collagenase activity and urokinase plasminogen activator expression (Laferriere, J. et al. *J. Biol. Chem.* 2001, 276, 33762-33772; Westermarck, J. et al. *Cancer Res.* 2000, 60, 7156-7162; Huang, S. et al. *J. Biol. Chem.* 2000, 275, 12266-12272; Simon, C. et al. *Exp. Cell Res.* 2001, 271, 344-355).

The receptor tyrosine kinase TrkA is another target of interest for the preparation of medicines directed at the treatment and prevention of cancer. TrkA is the high affinity receptor of the nerve growth factor (NGF). The expression of TrkA and NGF in tumors is believed to be implicated in the proliferation and metastasis of tumors such as pancreatic, prostate and also breast, as well as in angiogenesis. TrkA expression is reported in pancreatic, breast, ovarian, and prostate tumors. Recent studies demonstrate that human prostate and pancreatic tumor cells can secrete NGF, which, along with its receptor, TrkA, creates an autocrine loop that promotes the growth and survival of these tumor cells (Ruggeri, B. A. et al, *Curr. Med. Chem.* 1999, 6:845-857; Weeraratna, A. T. et al., *The Prostate* 2000, 45:140-148). Inhibition of the NGF-TrkA signaling pathway by small molecule TrkA inhibitors (Miknyoczki, S. J. et al., *Clin. Cancer Res.* 1999, 5: 2205-2212; George, D. J. et al., *Cancer Res.* 1999, 59: 2395-2401; Weeraratna, A. T. et al, *Clin. Cancer Res.* 2001, 7: 2237-2245) and anti-NGF antibodies (Miknyoczki, S. J. et al., *Clin. Cancer Res.* 2002, 8:1924-1931) has been postulated to inhibit not only growth, but also metastasis of neuroendocrine tumors in xenograft models. In addition, NGF has been shown to induce proliferation of endothelial cells (Cantarella, G. et al., *FASEB J.* 2002, 16:1307). These cells, which form new vascular networks to feed the growing tumor, also express VEGFR2 tyrosine kinase receptors. Activation of these receptors by their ligands leads to endothelial cell proliferation, migration, and vessel formation and stabilization (Albo, D. et al., *Curr. Pharm. Des.* 2004, 10:27-37; Thurston, G., *Cell Tissue Res.* 2003, 31:61-68).

The proto-oncogene c-Met, a member of the receptor tyrosine kinase family, encodes a heterodimeric complex consisting of a 140-kDa membrane-spanning β chain and a 50-kDa extracellular α chain. This heterodimeric complex acts as a high-affinity receptor for hepatocyte growth factor (HGF) or scatter factor (SF). c-Met/HGF signaling is required for normal mammalian development and has been shown to be particularly important in cell growth, migration, morphogenic differentiation, and organization of three-dimensional tubular structures (e.g. renal tubular cells, gland formation, etc.). c-Met and HGF are widely expressed in a variety of tissues, and their expression is normally confined to cells of epithelial and mesenchymal origin, respectively. There are now several lines of compelling evidence that HGF/c-Met signaling has an important role in the development and malignant progression of tumors of various histological types. Cell lines that ectopically overexpress c-Met or HGF become tumorigenic and metastatic in nude mice, whereas c-Met downregulation decreases their tumorigenic potential. HGF-dependent autocrine loops are found associated with osteosarcomas, rhabdomyosarcomas and breast carcinomas (Trusolino and Comoglio, *Nat Rev Cancer,* 2002, 2, 289-300). c-Met or HGF transgenic mice develop metastatic tumors (Wang, R. et al., *J. Cell Biol.* 2001, 153, 1023-1034; Takayama et al., *Proc. Natl. Acad. Sci. U.S.A.* 1997, 94, 701-706). Over-expression of c-Met expression has been found in many kinds of solid tumors and correlates with poor prognosis (Birchmeier, et al. *Mol. Cell. Biol.,* 2003, 4, 915-925; Christensen, J. and Salgia, R., *Can Lett.,* 2005, 225, 1-26). The unequivocal evidence linking c-Met and human cancer comes from the identification of germline activating mutations in patients suffering from hereditary papillary renal carcinomas (Dharmawardana, et al., *Curr. Mol. Med.,* 2004, 4, 855-868). Finally, amplification of the c-Met gene was observed in many gastric tumors (Ponzetto, C. et al., *Oncogene.* 1991, 6, 553-9).

Due to a strong link between c-Met/HGF signaling pathway and tumorigenesis and tumor progression, several therapeutic approaches have been pursued by various groups. HGF/SF-neutralizing antibodies (Cao et al., *Proc Natl Acad Sci USA* 2001, 98, 7443-8), c-Met antisense oligonucleotides (Kitamura et al., *Br J Cancer* 2000, 83: 668-73), dominant-negative forms of the Met protein (Firon et al., *Oncogene* 2000, 19, 2386-97; Furge et al., *Proc Natl Acad Sci USA* 2001, 98, 10722-7), ribozymes that target Met mRNA (Abounader et al., *J Natl Cancer Inst,* 1999, 91, 1548-56; Abounader et al., *FASEB J* 2002, 16, 108-10), and small molecule c-Met kinase inhibitors (Christensen et al., *Cancer Res* 2003, 63, 7345-55) are being investigated as possible strategies to block c-Met activation and suppress tumor growth, invasion, and metastasis. Identification of a potent inhibitor of c-Met kinase activity therefore has the great potential to inhibit tumor growth of various cancer types.

Chronic myelogenous leukemia (CML) is caused by the oncogenic protein, Bcr-Abl (Groffen, J. et al., *J Cell Physiol Suppl,* 1984, 3, 179-191, Sattler, M. and Griffin, J. D., *Semin Hematol,* 2003, 40, 4-10). The Philadelphia chromosome, which is the hallmark of CML, is formed in CML patients due to a reciprocal translocation between chromosomes 9 and 22 (Rowley, J. D., *Nature,* 1973, 243, 290-293), and this translocation results in the formation of Bcr-Abl fusion protein (Groffen, J. and Heisterkamp, N., *Baillieres Clin Haematol,* 1987, 1, 983-999). Abl protein is a non-receptor tyrosine kinase whose activity is tightly regulated in normal cells. However, the Bcr-Abl fusion protein is constitutively activated due to the presence of Bcr protein at the N-terminus. The constitutively active protein transforms at the myeloid blast cell stage thus giving rise to CML (Kelliher, M. A., et al., *Proc Natl Acad Sci USA,* 1990, 87, 6649-6653). Depending on the exact breakpoints at the chromosomes involved in the translocation, the size of the fusion protein varies from 185 to 230 kDa, although 210 kDa protein is the most common in CML.

Development of Imatinib (Gleevec®, ST1571) as an inhibitor of Bcr-Abl protein to treat CML patients has pioneered the field of targeted therapy in oncology (Capdeville, R., et al., *Nat Rev Drug Discov,* 2002, 1, 493-502). Patients with early phase CML were found to respond to a degree of greater than 90% at both haematological and cytogenetic levels (Deininger, M. et al., *Blood,* 2005, 105, 2640-2653, Talpaz, M. et al., *Blood,* 2002, 99, 1928-1937). However, most patients develop resistance to Imatinib after prolonged treatment (Gorre, M. E. and Sawyers, C. L., *Curr Opin Hematol,* 2002, 9, 303-307). To date, more than 30 Imatinib-resistant mutations of Bcr-Abl have been observed in patients and most of these mutations are confined to a sub-domain within the kinase region of the fusion protein. Importantly, three mutations namely T315I, E255K and M351T represent more than 50% of the Imatinib resistance (Deininger, M., Buchdunger, E. and Druker, B. J., *Blood,* 2005, 105, 2640-2653).

Recently, there has been much effort to overcome the Imatinib resistance in CML patients. For example, BMS-354825 (dasatinib) has been reported to be an inhibitor of Bcr-Abl and also Src family kinases. Among the 15 Imatinib-resistant Bcr-Abl mutations tested in cell based assays, BMS-354825 was reported to inhibit all the mutant forms of the protein, except T315I (Shah, N. P., et al., *Science,* 2004, 305, 399-401). The compound AMN-107 (nilotinib) has been reported to inhibit Bcr-Abl kinase activity with 20-fold greater potency than Imatinib. AMN-107 was reported to inhibit most Imatinib-resistant Bcr-Abl mutations, except for T315I. AMN-107 also shows somewhat weak inhibition in a biochemical assay against the E255K mutant (Weisberg, E., et al., *Cancer Cell,* 2005, 7, 129-141). Therefore, there is a significant unmet medical need for new therapeutics to treat CML and Imatinib-resistant CML.

Certain diaryl ureas have been described as having activity as serine-threonine kinase and/or tyrosine kinase inhibitors. The utility of these diaryl ureas as an active ingredient in pharmaceutical compositions for the treatment of cancer, angiogenesis disorders, and inflammatory disorders has been demonstrated. See Redman et al., *Bioorg. Med. Chem. Lett.* 2001, 11, 9-12; Smith et al., *Bioorg. Med. Chem. Lett.* 2001, 11, 2775-2778; Dumas et al., *Bioorg. Med. Chem. Lett.* 2000, 10, 2047-2050; Dumas et al., *Bioorg. Med. Chem. Lett.* 2000, 10, 2051-2054; Ranges et al., *Book of Abstracts,* 220th *ACS National Meeting,* 2000, *Washington, D.C., USA, MEDI* 149; Dumas et al., *Bioorg. Med. Chem. Lett.* 2002, 12, 1559-1562; Lowinger et al., *Clin. Cancer Res.* 2000, 6 (suppl.), 335; Lyons et al., *Endocr.-Relat. Cancer* 2001, 8, 219-225; Riedl et al., *Book of Abstracts,* 92nd *AACR Meeting,* 2001, *New Orleans, La., USA,* abstract 4956; Khire et al., *Book of Abstracts,* 93rd*AACR Meeting,* 2002, *San Francisco, Calif., USA,* abstract 4211; Lowinger et al., *Curr. Pharm. Design* 2002, 8, 99-110; Regan et al., *J. Med. Chem.* 2002, 45, 2994-3008; Pargellis et al., *Nature Struct. Biol.* 2002, 9 (4), 268-272; Carter et al., *Book of Abstracts,* 92nd*AACR Meeting,* 2001, *New Orleans, La., USA,* abstract 4954; Vincent et al., *Book of Abstracts,* 38th *ASCO Meeting,* 2002, *Orlando, Fla.,*

USA, *abstract* 1900; Hilger et al., *Book of Abstracts, 38th ASCO Meeting,* 2002, *Orlando, Fla., USA, abstract* 1916; Moore et al., *Book of Abstracts, 38th ASCO Meeting,* 2002, *Orlando, Fla., USA, abstract* 1816; Strumberg et al., *Book of Abstracts, 38th ASCO Meeting,* 2002, *Orlando, Fla., USA, abstract* 121; Madwed, *Book of Abstracts, Protein Kinases: Novel Target Identification and Validation for Therapeutic Development, San Diego, Calif., USA,* 2002; Roberts et al., *Book of Abstracts, 38th ASCO Meeting,* 2002, *Orlando, Fla., USA, abstract* 473; Tolcher et al., *Book of Abstracts, 38th ASCO Meeting,* 2002, *Orlando, Fla., USA, abstract* 334; and Karp et al., *Book of Abstracts, 38th AACR Meeting, San Francisco, Calif., USA, abstract* 2753.

Certain urea derivatives, including certain pyrazolyl phenyl ureas, have been identified as effective inhibitors of protein kinases such as raf kinase and p38 kinase, and these compounds were described in Dumas, J. et al., "Inhibition of p38 Kinase Activity using Aryl- and Heteroaryl-Substituted Heterocyclic Ureas", PCT Int. Appl., WO 99 32110; and Dumas, J. et al., "Inhibition of Raf Kinase using Aryl- and Heteroaryl Substituted Heterocyclic Ureas", PCT Int. Appl., WO 99 32455. One pyrazolyl phenyl urea compound of interest in WO 99 32110 is Example 37, namely 1-[5-tert-butyl-2-(4-fluoro-phenyl)-2H-pyrazol-3-yl]-3-[4-(pyridin-4-yloxy)-phenyl]-urea. Related pyrazole compounds of interest were also described in Regan, J. R. et al., "Aromatic Heterocyclic Compounds as Anti-Inflammatory Agents", PCT Int. Appl., WO 99 23091. More recently, certain pyrazolyl phenyl ureas having functionalized "tail groups" as substituents on the pyrazolyl-N-phenyl group, were discovered to be effective protein kinase inhibitors, with activities against VEGFR2, PDGFR, and Trk-A, for example; these compounds were described in Lee, W. et al., "Substituted Pyrazolyl Urea Derivatives Useful in the Treatment of Cancer", PCT Int. Appl., WO 2005 110994. Other pyrazolyl phenyl urea compounds of interest were recently discovered to be effective inhibitors of, for example, VEGFR2, c-Met, Bcr-Abl, and various mutations of Bcr-Abl, and these compounds were described in Smith, R. et al., "Urea Compounds Useful in the Treatment of Cancer", PCT Int. Appl. US/0645976, filed Dec. 1, 2006, WO 2007/064872 entitled, "Urea Compounds Useful in the Treatment of Cancer." Compounds of interest in this same patent application from Smith, R. et al. incorporate a 4-(4-amino-phenoxy)-pyridine-2-carboxylic acid methylamide fragment, or 4-(4-amino-3-fluoro-phenoxy)-pyridine-2-carboxylic acid methylamide fragment, or 4-(4-Amino-3-fluoro-phenoxy)-pyridine-2-carboxylic acid amide fragment, for example. Related pyrazole compounds of interest were also described in Hoelzemann, G. et al., "Pyrazole Derivatives", PCT Int. Appl., WO 2006/105844. The compound and compositions of the current invention are of particular interest, as they exhibit potent activities against, for example, VEGFR2, wild-type Bcr-Abl, and various mutations of Bcr-Abl, as well as desirable physicochemical properties such as solubility in aqueous and organic media and desirable in vivo pharmacokinetics and pharmacological profiles.

Despite advancements in the art, there remains a need for cancer treatments and anti-cancer compounds.

The utility of the compounds of the present invention can be illustrated, for example, by their activity in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11 (6), 528-35), taxotere (Bissery et al. *Anti Cancer Drugs* 1995, 6 (3), 339), and topoisomerase inhibitors (Edelman et al. *Cancer Chemother. Pharmacol.* 1996, 37 (5), 385-93) were demonstrated with the use of in vitro tumor proliferation assays.

Compounds and compositions described herein, including salts and esters thereof, exhibit anti-proliferative activity and are thus useful to prevent or treat the disorders associated with hyper-proliferation.

DESCRIPTION OF THE INVENTION

It has been discovered that the novel hydroxyl phenyl pyrazolyl urea compounds are potent inhibitors of VEGFR kinase, wild-type Bcr-Abl, and various mutations of Bcr-Abl including T315I, which are all molecular targets of interest for the treatment of proliferative diseases, including cancer.

The present invention pertains to: (i) the novel compound: 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide and the salts, solvates, hydrates, prodrugs, polymorphs and metabolites thereof, including diastereoisomeric forms of the salts and prodrugs thereof, both as an isolated stereoisomer and forms within a mixture of stereoisomers;

(ii) pharmaceutical compositions of the novel compound: 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide or a salt, solvate hydrate, prodrug, polymorph, or metabolite thereof (including diastereoisomeric forms of the salts and prodrugs thereof), and (iii) the use of (i) or (ii) for treating hyper-proliferative and angiogenesis disorders, as sole agents or in combination with cytotoxic therapies.

The compound 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide and the salts, hydrates, solvates, prodrugs, polymorphs and metabolites thereof (including the diastoeroisomeric forms of salts and prodrugs) are collectively referred to as the "compounds of the invention".

The metabolites of the compound (4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide) and other compounds of this invention include oxidized derivatives thereof wherein one or more of the nitrogens are substituted with a hydroxy group. The metabolites also include analogs of the compound 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide and other compounds of this invention where the methylamide group is de-methylated by metabolic degradation. The metabolites further include oxidized derivatives of the compound: (4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide) and other compounds of this invention where the nitrogen atom of the pyridine group may be in the oxide form (or have a hydroxy substituent) and includes those structures referred to in the art as 1-oxo-pyridine and 1-hydroxy-pyridine.

Where the plural form of the word compounds, salts, and the like, is used herein, this is taken to mean also a single compound, salt, or the like.

The use of pharmaceutically acceptable salts of (4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide) and other compounds of this invention is also within the scope of this invention. The term "pharmaceutically acceptable salt" refers to a relatively non-toxic, inorganic or organic acid addition salt. For example, see S. M. Berge, et al. "Pharmaceutical Salts," *J. Pharm. Sci.* 1977, 66, 1-19.

Representative salts of the compound 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide and other compounds of this invention include the conventional non-toxic salts, for example, from inorganic or organic acids by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Solvates for the purpose of this invention are those forms of the compounds of this invention where solvent molecules form a complex in the solid state and include, but are not limited to for example ethanol and methanol. Hydrates are a specific form of solvates where the solvent is water.

The compound 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide and other compounds of this invention can be further modified with labile functional groups that are cleaved after in vivo administration to furnish the parent active agent and the pharmacologically inactive derivatizing (functional) group. These derivatives, commonly referred to as prodrugs, can be used, for example, to alter the physicochemical properties of the active agent, to target the active agent to a specific tissue, to alter the pharmacokinetic and pharmacodynamic properties of the active agent, and to reduce undesirable side effects.

Prodrugs of the compound 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide and other compounds of the current invention include, for example, well-tolerated and pharmaceutically acceptable esters that can be prepared by acylation of the hydroxyl group. Examples of such ester prodrugs include the esters prepared from acetic, propionic, butyric, isobutyric, valeric, isovaleric, succinic and methoxyacetic acid. Additional examples of ester prodrugs include the esters prepared from amino acids such as D-alanine, L-alanine, D-valine, L-valine, beta-alanine, and the like. Other examples of ester prodrugs include the phosphate esters that can be prepared via the bis(tert-butyl)phosphate esters.

Methods for synthesizing prodrugs are described in the following reviews on the subject, which are incorporated herein by reference for their description of these methods: Higuchi, T.; Stella, V. eds. *Prodrugs As Novel Drug Delivery Systems*. ACS Symposium Series. American Chemical Society: Washington, D.C. (1975); Roche, E. B. *Design of Biopharmaceutical Properties through Prodrugs and Analogs.* American Pharmaceutical Association Washington, D.C. (1977); Sinkula, A. A.; Yalkowsky, S. H. *J Pharm Sci.* 1975, 64, 181-210; Stella, V. J.; Charman, W. N. Naringrekar, V. H. *Drugs* 1985, 29, 455-473; Bundgaard, H., ed. *Design of Prodrugs*. Elsevier: New York (1985); Stella, V. J.; Himmelstein, K. J. *J. Med. Chem.* 1980, 23, 1275-1282; Han, H-K; Amidon, G. L. *AAPS Pharmsci* 2000, 2, 1-11; Denny, W. A. *Eur. J. Med. Chem.* 2001, 36, 577-595; Wermuth, C. G. in Wermuth, C. G. ed. *The Practice of Medicinal Chemistry* Academic Press: San Diego (1996), 697-715; Balant, L. P.; Doelker, E. in Wolff, M. E. ed. *Burgers Medicinal Chemistry And Drug Discovery* John Wiley & Sons: New York (1997), 949-982.

The salts or prodrugs of the compounds of this invention may contain one or more asymmetric centers. Asymmetric carbon atoms may be present in the (R) or (S) configuration or (R,S) configuration. Substituents on a ring may also be present in either cis or trans form. It is intended that all such configurations (including enantiomers and diastereomers), are included within the scope of the present invention. Preferred isomers are those with the configuration which produces the more desirable biological activity. Separated, pure or partially purified isomers or racemic mixtures of the compounds of this invention are also included within the scope of the present invention. The purification of said isomers and the separation of said isomeric mixtures can be accomplished by standard techniques known in the art.

A particular process to prepare the compound 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide is described in Example 1. The preparation of salt forms are described in Examples 2 to 7.

The compound of Example 1 (4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide) may be prepared by alternative methods. Specific preparations of diaryl ureas, including pyrazolyl ureas, are already described in the patent literature, and can be adapted to the compounds of the present invention. For example, Miller S. et al, "Inhibition of p38 Kinase using Symmetrical and Unsymmetrical Diphenyl Ureas" PCT Int. Appl. WO 99 32463; Miller, S et al. "Inhibition of raf Kinase using Symmetrical and Unsymmetrical Substituted Diphenyl Ureas" PCT Int. Appl., WO 99 32436; Dumas, J. et al., "Inhibition of p38 Kinase Activity using Substituted Heterocyclic Ureas" PCT Int. Appl., WO 99 32111; Dumas, J. et al., "Method for the Treatment of Neoplasm by Inhibition of raf Kinase using N-Heteroaryl-N'-(hetero)arylureas" PCT Int. Appl., WO 99 32106; Dumas, J. et al., "Inhibition of p38 Kinase Activity using Aryl- and Heteroaryl-Substituted Heterocyclic Ureas" PCT Int. Appl., WO 99 32110; Dumas, J., et al., "Inhibition of raf Kinase using Aryl- and Heteroaryl-Substituted Heterocyclic Ureas" PCT Int. Appl., WO 99 32455; Riedl, B., et al., "O-Carboxy Aryl Substituted Diphenyl Ureas as raf Kinase Inhibitors" PCT Int. Appl., WO 2000 42012; Riedl, B., et al., "O-Carboxy Aryl Substituted Diphenyl Ureas as p38 Kinase Inhibitors", PCT Int. Appl., WO 2000 41698; Dumas, J. et al. "Heteroaryl ureas containing nitrogen hetero-atoms as p38 kinase inhibitors", U.S. Pat. Appl. Publ., US 20020065296; Dumas, J. et al., "Preparation of N-aryl-N'-[(acylphenoxy) phenyl]ureas as raf kinase inhibitors", PCT Int. Appl., WO 2002 62763; Dumas, J. et al., "Inhibition of raf kinase using quinolyl, isoquinolyl or pyridyl ureas", PCT Int. Appl., WO 2002 85857; Dumas, J. et al., "Preparation of quinolyl, isoquinolyl or pyridyl-ureas as inhibitors of raf kinase for the treatment of tumors and/or cancerous cell growth" U.S. Pat. Appl. Publ., US 20020165394; Lee, W. et al., "Substituted Pyrazolyl Urea Derivatives Useful in the Treatment of Cancer", PCT Int. Appl., WO 2005 110994. All of the preceding patent applications are hereby incorporated by reference.

Synthetic transformations that may be employed in the synthesis of the compound of this invention and in the synthesis of intermediates involved in the synthesis of the compound of this invention are known by or accessible to one skilled in the art. Collections of synthetic transformations may be found in compilations, such as:

J. March. *Advanced Organic Chemistry,* 4th ed.; John Wiley: New York (1992)

R. C. Larock. *Comprehensive Organic Transformations,* 2nd ed.; Wiley-VCH: New York (1999)

F. A. Carey; R. J. Sundberg. *Advanced Organic Chemistry,* 2nd ed.; Plenum Press: New York (1984)

T. W. Greene; P. G. M. Wuts. *Protective Groups in Organic Synthesis,* 3rd ed.; John Wiley: New York (1999)

L. S. Hegedus. *Transition Metals in the Synthesis of Complex Organic Molecules,* 2nd ed.; University Science Books: Mill Valley, Calif. (1994)

L. A. Paquette, Ed. *The Encyclopedia of Reagents for Organic Synthesis*; John Wiley: New York (1994)

A. R. Katritzky; O. Meth-Cohn; C. W. Rees, Eds. *Comprehensive Organic Functional Group Transformations*; Pergamon Press: Oxford, UK (1995)

G. Wilkinson; F. G A. Stone; E. W. Abel, Eds. *Comprehensive Organometallic Chemistry*; Pergamon Press: Oxford, UK (1982)

B. M. Trost; I. Fleming. *Comprehensive Organic Synthesis*; Pergamon Press: Oxford, UK (1991)

A. R. Katritzky; C. W. Rees Eds. *Comprehensive Heterocylic Chemistry*; Pergamon Press: Oxford, UK (1984)

A. R. Katritzky; C. W. Rees; E. F. V. Scriven, Eds. *Comprehensive Heterocylic Chemistry II*; Pergamon Press: Oxford, UK (1996)

C. Hansch; P. G. Sammes; J. B. Taylor, Eds. *Comprehensive Medicinal Chemistry*: Pergamon Press: Oxford, UK (1990).

In addition, recurring reviews of synthetic methodology and related topics include *Organic Reactions*; John Wiley: New York; *Organic Syntheses*; John Wiley: New York; *Reagents for Organic Synthesis*: John Wiley: New York; *The Total Synthesis of Natural Products*; John Wiley: New York; *The Organic Chemistry of Drug Synthesis*; John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include *Chemical Abstracts*, which may be searched using either CAS OnLine or SciFinder, *Handbuch der Organischen Chemie* (Beilstein), which may be searched using SpotFire, and REACCS.

The present invention also relates to methods of screening patients to determine their susceptibility to compounds of the present invention. For example, the present invention relates to methods of selecting subjects having a disease for treatment comprising, one or more of the following steps in any effective order, e.g., measuring the expression or activity of Flk-1, Trk-A, c-Met, and/or Bcr-Abl, in a sample obtained from a subject having a disease, and administering a compound of this invention to subjects who are identified as having altered (e.g., high or activating) levels of expression or activity.

The term "susceptibility" is used broadly to indicate, e.g., ability to respond, toxicity or other adverse effects, etc. For example, the invention relates to methods of determining whether a condition can be modulated by a compound disclosed herein, comprising measuring the expression or activity of Flk-1, Trk-A, c-Met, and/or Bcr-Abl in cells having said condition. The results can be used to determine or predict whether a subject will respond to a compound of the present invention. For example, where the condition is a tumor, the methods can be used to predict whether the tumor is susceptible to compounds of the present invention. By the term "susceptible," it is meant that tumor can be treated with it, e.g., causing tumor regression or cell death, inhibiting cell proliferation, inhibiting tumor growth, inhibiting tumor metastasis, etc.

Whether a condition, such as a tumor, is susceptible to a compound of the present invention can be determined routinely. For instance, cells or tissues (e.g., tumor cells, a biopsy sample, etc.) that exhibit the condition can be assayed for the presence and/or absence of Flk-1, Trk-A, c-Met, and/or Bcr-Abl activity, and levels thereof. When aberrant (e.g., high) levels of expression and/or activity are identified, this can indicate that the subject will respond to, and benefit from, a compound of the present invention. Levels of gene expression (e.g., mRNA levels), gene amplification, or gene product activity (e.g., tyrosine kinase activity) can be utilized to characterize the state of the cell with respect to the corresponding gene and signaling pathway. For example, the target genes of the present invention possess tyrosine kinase activity, and therefore kinase activity can be used to assess the cell or tissue state. In the example below, activity was measured by looking at the levels of substrate phosphorylated by it. This can be done quantitatively (e.g., using isotopes, spectroscopy, etc.) or semi-quantitatively as in the example where the levels were assessed visually and assigned a level of intensity from +1 to +4. For example, a cell or tissue which has a high level of phosphorylated substrate (and a high number of cells exhibiting the heightened activity) can be considered to have a high level of kinase activity, and therefore be a candidate for therapy with a compound of the present invention. More than one activity can be assessed, and the results from several targets can be utilized in deciding whether a subject's condition (e.g., a tumor) will be responsive to a compound of the present invention.

Levels of target activity can be relative to a control or other standard. For example, "high" levels can therefore be where cells express a statistically higher amount of measured activity or phosphorylated substrate than the standard or control used as a comparison. High levels can also be where 25% or more cells express the target activity.

The method can further comprise a step of comparing the expression in a sample with a normal control, or expression in a sample obtained from normal or unaffected tissue. Comparing can be done manually, against a standard, in an electronic form (e.g., against a database), etc. The normal control can be a standard sample that is provided with the assay; it can be obtained from adjacent, but unaffected, tissue from the same patient; or, it can be pre-determined values, etc. Gene expression, protein expression (e.g., abundance in a cell), protein activity (e.g., kinase activity), etc., can be determined.

For instance, a biopsy from a cancer patient can be assayed for the presence, quantity, and/or activity of Flk-1, Trk-A, c-Met, and/or Bcr-Abl. Aberrant (e.g., increased) expression or activity of one or more of these can indicate that the cancer can be targeted for treatment by a compound of the present invention. Increased kinase activity indicates that the corresponding kinase is either activated or over-expressed, suggesting the use of compounds of the present invention to treat it. In addition to biopsy samples, expression can also be measured in other body fluids, such as serum, blood, cerebral spinal fluid, urine, etc., such as in peripheral blood lymphocytes (PBLs).

In addition, patients having cancer can be selected and monitored on the basis of whether the tissue is experiencing neovacularization, and how much. This can be assessed as discussed above, e.g., using immunohistochemistry for vessel markers (e.g., CD31), circulating levels of a VGFR ligand, etc.

Patient selection and monitoring can also be made on the basis of the appearance in a body fluid (such as blood) above normal levels of the shedded ectodomains derived from the various receptors, including the extracellular portions of Flk-1, Trk-A, c-Met, and/or Bcr-Abl. Detection methods can be carried out routinely, e.g., using antibodies which specifically bind to the extracellular domain. Measuring expression includes determining or detecting the amount of the polypeptide present in a cell or shed by it, as well as measuring the underlying mRNA, where the quantity of mRNA present is considered to reflect the quantity of polypeptide manufactured by the cell. Furthermore, the genes for Flk-1, Trk-A, c-Met, and/or Bcr-Abl can be analyzed to determine whether there is a gene defect responsible for aberrant expression or polypeptide activity. Sequences for these genes are publicly available.

Compositions of the Compounds of this Invention

This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of a compound of the present invention. These compositions can be prepared by mixing a compound of the present invention with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52 (5), 238-311; Strickley, R. G "Parenteral Formulations of Small Molecule Therapeutics Marketed in the United States (1999)—Part-1" *PDA Journal of Pharmaceutical Science & Technology* 1999, 53 (6), 324-349; and Nema, S. et al, "Excipients and Their Use in Injectable Products" *PDA Journal of Pharmaceutical Science & Technology* 1997, 51 (4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized powder for IV administration: A sterile preparation can be prepared with (i) 100-1000 mg of the desired compound of this invention as a lyophilized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:
50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Hyper-Proliferative Disorders

The present invention relates to a method for using the compounds of the present invention and compositions thereof, to treat mammalian hyper-proliferative disorders. The compounds and compositions of this invention can be utilized to inhibit, block, reduce, decrease, etc., cell proliferation and/or cell division, and/or produce apoptosis. This method comprises administering to a mammal in need thereof, including a human, an amount of a compound of this invention, which is effective to treat the disorder. Hyper-proliferative disorders include but are not limited to, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this discussed is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant kinase activity (such as tyrosine kinase activity), including, but not limited to KDR (VEGFR2), Trk-A, c-Met, and Bcr-Abl, comprising administering an effective amount of a compound of the present invention. Disorders include cancers (such as those mentioned herein), disorders associated with angiogenesis (see above), cell proliferation disorders, etc. For example, c-Met over-expression and mutations have been found in many tumor types, including, e.g., solid tumors, hereditary papillary renal carcinoma, heptatocellular carcinoma (e.g., childhood type), and gastric tumors. Trk-A expression and mutations have been reported in cancers, including, e.g., pancreatic, breast, ovarian, prostate carcinoma, papillary thyroid carcinoma, medullary thyroid carcinoma (including familial forms), and acute myeloid leukemia. Bcr-Abl and mutations of this kinase are the cause of chronic myelogenous leukemia (CML).

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of VEGFR2, Trk-A, c-Met, and/or Bcr-Abl comprising administering an effective amount of a compound of the present invention, including salts, polymorphs, metabolites, hyrates, solvates, prodrugs (e.g.: esters) thereof, and diastereoisomeric forms thereof). Kinase activity can be inhibited in cells (e.g., in vitro), or in the cells of a mammalian subject, especially a human patient in need of treatment.

Compounds of the present invention can be used for any of the indications described in U.S. Pat. Nos. 6,946,471; 6,921,763; 6,855,728; 6,723,694; 6,660,744; 6,468,529; 6,350,754; 6,297,238; 6,214,344; 6,207,152; 6,099,841; 6,057,105; 6,051,593; 5,734,039; 5,707,624; 5,686,292; and 5,646,036; each of which is incorporated by reference in its entirety.

Methods of Treating Angiogenic Disorders

The present invention also provides methods of treating disorders and diseases associated with excessive and/or abnormal angiogenesis. Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity (Aiello et al. *New Engl. J. Med.* 1994, 331, 1480; Peer et al. *Lab. Invest.* 1995, 72, 638), age-related macular degeneration (AMD; see, Lopez et al. Invest. Opththalmol. Vis. Sci. 1996, 37, 855), neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Compounds and compositions of the present invention can be tested routinely for angiogenic activity, e.g., by contacting a blood vessel-forming cell population with a compound of the present invention, and determining the effect of the compound on blood vessel formation. Any cell population capable of forming blood vessels can be utilized. Useful models, include, e.g., in vivo Matrigel-type assays; tumor neovascularization assays; CAM assays; BCE assays; cell migration assays; HUVEC growth inhibition assays; animal models (e.g., tumor growth in athymic mice, chronically ischemic lower limb in a rabbit model, cancer models, etc.); in vivo systems, such as a heart or limb present in a patient (e.g., angiogenic therapy to treat myocardial infarction); hosts in need of treatment, e.g., hosts suffering from angiogenesis related diseases, such as cancer, ischemic syndromes, arterial obstructive disease, to promote collateral circulation, to promote vessel growth into bioengineered tissues, etc.

Cells can include, e.g., endothelial, epithelial, muscle, embryonic and adult stem cells, ectodermal, mesenchymal, endodermal, neoplastic, blood, bovine CPAE (CCL-209), bovine FBHE (CRL-1395), human HUV-EC-C(CRL-1730), mouse SVEC4-10EHR1 (CRL-2161), mouse MS1 (CRL-2279), mouse MS1 VEGF (CRL-2460), stem cells, etc. The phrase "capable of forming blood vessels" does not indicate a particular cell-type, but simply that the cells in the population are able under appropriate conditions to form blood vessels. In some circumstances, the population may be heterogeneous, comprising more than one cell-type, only some which actually differentiate into blood vessels, but others which are necessary to initiate, maintain, etc., the process of vessel formation.

A useful model to determine the effect of compounds or compositions on angiogenesis is based on the observation that, when a reconstituted basement membrane matrix, such as Matrigel, supplemented with growth factor (e.g., FGF-1), is injected subcutaneously into a host animal, endothelial cells are recruited into the matrix, forming new blood vessels over a period of several days. See, e.g., Passaniti et al., Lab. Invest., 67:519-528, 1992. To stabilize the growth factor and/or slow its release from the matrix, the growth factor can be bound to heparin or another stabilizing agent. The matrix can also be periodically re-infused with growth factor to enhance and extend the angiogenic process. More specifically, a Matrigel plug implant comprising FGF-1 can be implanted subcutaneously into a host mouse. The initial bolus of FGF attracts endothelial cells into the implant, but does not result in new blood vessel formation. After about 10-15 days, the implant can be re-infused with FGF-1. The FGF-1 stimulates the endothelial cells already present in the implant, initiating the process of angiogenesis.

Other useful systems for studying angiogenesis, include, e.g., neovascularization of tumor explants (e.g., U.S. Pat. Nos. 5,192,744; 6,024,688), chicken chorioallantoic membrane (CAM) assay (e.g., Taylor and Folkman, Nature, 297: 307-312, 1982; Eliceiri et al., J. Cell Biol., 140, 1255-1263, 1998), bovine capillary endothelial (BCE) cell assay (e.g., U.S. Pat. No. 6,024,688; Polyerini, P. J. et al., Methods Enzymol., 198: 440-450, 1991), migration assays, HUVEC (human umbilical cord vascular endothelial cell) growth inhibition assay (e.g., U.S. Pat. No. 6,060,449).

A cell population can be contacted with a compound or composition of this invention in any manner and under any conditions suitable for it to exert an effect on the cells. The means by which compound is delivered to the cells may depend upon the type of test agent, e.g., its chemical nature, and the nature of the cell population. Generally, a compound must have access to the cell population, so it must be delivered in a form (or pro-form) that the population can experience physiologically, i.e., to put in contact with the cells. For instance, if the intent is for the agent to enter the cell, if necessary, it can be associated with any means that facilitate or enhance cell penetrance, e.g., associated with antibodies or other reagents specific for cell-surface antigens, liposomes, lipids, chelating agents, targeting moieties, etc. Cells can also be treated, manipulated, etc., to enhance delivery, e.g., by electroporation, pressure variation, etc.

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of a compound of this invention to be administered in the treatment of one of these conditions can vary widely according to such considerations as the particular compound and dosage unit employed, the mode of administration, the period of treatment, the age and sex of the patient treated, and the nature and extent of the condition treated.

The total amount of a compound of the present invention to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a compound of the present invention for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention can be ascertained by those skilled in the art using conventional treatment tests.

The compounds of this invention can be administered as the sole pharmaceutical agent or in combination with one or more other pharmaceutical agents where the combination causes no unacceptable adverse effects. For example, the compounds of this invention can be combined with known anti-hyper-proliferative or other indication agents, and the like, as well as with admixtures and combinations thereof.

"The additional pharmaceutical agent can be aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DAUNOXOME® (daunorubicin), decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, EPOGEN® (epotin-alpha), eptaplatin, ergamisol, estrace, estradiol, estramustine phosphate sodium, ethinyl estradiol, ethyol, etidronic acid, etopophos, etoposide, fadrozole, FARESTON® (Toremitene), filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, GLEEVEC® (imatinib mesylate), GLIADEL® (wafer), goserelin, granisetron HC1, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, INTRON-A (interferon alfa-2b, recombinant), iressa, irinotecan, kytril, lentinan sulphate, letrozole, leucovorin, leuprolide, leuprolide acetate, levamisole, levofolinic acid calcium salt, levothroid, LEVOXYL® (levothyroxine sodium tablets,), lomustine, lonidamine, marinol, mechlorethamine, mecobalamin, medroxyprogesterone acetate, megestrol acetate, melphalan, MENEST® (esterified estrogens) 6 mercaptopurine, Mesna, methotrexate, metvix, miltefosine, minocycline, mitomycin C, mitotane, mitoxantrone, MODRENAL® (trilostane), MYOCET® (non-pegylated liposomal doxorubicin), nedaplatin, neulasta, neumega, neupogen, nilutamide, NOLVADEX® (tamoxifen citrate), NSC-631570, OCT-43, octreotide, ondansetron HC1, orapred, oxaliplatin, paclitaxel, pediapred, pegaspargase, PEAGASYS (peginterferon alfa-2a), pentostatin, picibanil, pilocarpine HC1, pirarubicin, plicamycin, porfimer sodium, prednimustine, prednisolone, prednisone, PREMARIN® (conjugated estrogen tablets), procarbazine, procrit, raltitrexed, rebif, rhenium-186 etidronate, rituximab, roferon-A, romurtide, salagen, sandostatin, sargramostim, semustine, sizofiran, sobuzoxane, solumedrol, sparfosic acid, stem-cell therapy, streptozocin, strontium-89 chloride, synthroid, tamoxifen, tamsulosin, tasonermin, tastolactone, TAXOTERE® (docetaxel), teceleukin, temozolomide, teniposide, testosterone propionate, TESTRED® (Methyltestosterone), thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, ZOFRAN® (ondansetron), ABI-007, acolbifene, actimmune, affinitak, aminopterin, arzoxifene, asoprisnil, atamestane, atrasentan, BAY 43-9006 (sorafenib), avastin, CCI-779, CDC-501, CELEBREX® (anti-inflamatory), cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis -retinoic acid, satraplatin, seocalcitol, T-138067, TARCEVA® (erlotinib), taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Optional anti-hyper-proliferative agents which can be added to the composition include but are not limited to compounds listed on the cancer chemotherapy drug regimens in the 11$^{th}$ Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with a compound or composition of the invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with a compound or composition of the invention include but are not limited to other anti-cancer agents such as epothilone and its derivatives, irinotecan, raloxifen and topotecan. Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemo-therapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Polypeptide detection can be carried out by any available method, e.g., by Western blots, ELISA, dot blot, immunoprecipitation, RIA, immunohistochemistry, etc. For instance, a tissue section can be prepared and labeled with a specific antibody (indirect or direct and visualized with a microscope. Amount of a polypeptide can be quantitated without visualization, e.g., by preparing a lysate of a sample of interest, and then determining by ELISA or Western the amount of polypeptide per quantity of tissue. Antibodies and other specific binding agents can be used. There is no limitation on how detection is performed.

Assays can be utilized which permit quantification and/or presence/absence detection of a target nucleic acid (e.g., genes, mRNA, etc., for Flk-1, Trk-A, c-Met, and/or Bcr-Abl, etc) in a sample. Assays can be performed at the single-cell level, or in a sample comprising many cells, where the assay is "averaging" expression over the entire collection of cells and tissue present in the sample. Any suitable assay format can be used, including, but not limited to, e.g., Southern blot analysis, Northern blot analysis, polymerase chain reaction ("PCR") (e.g., Saiki et al., Science, 241:53, 1988; U.S. Pat. Nos. 4,683,195, 4,683,202, and 6,040,166; PCR Protocols: A Guide to Methods and Applications, Innis et al., eds., Academic Press, New York, 1990), reverse transcriptase polymerase chain reaction ("RT-PCR"), anchored PCR, rapid amplification of cDNA ends ("RACE") (e.g., Schaefer in Gene Cloning and Analysis: Current Innovations, Pages 99-115, 1997), ligase chain reaction ("LCR") (EP 320 308), one-sided PCR (Ohara et al., Proc. Natl. Acad. Sci., 86:5673-5677, 1989), indexing methods (e.g., U.S. Pat. No. 5,508,169), in situ hybridization, differential display (e.g., Liang et al., Nucl. Acid. Res., 21:3269 3275, 1993; U.S. Pat. Nos. 5,262,311, 5,599,672 and 5,965,409; WO97/18454; Prashar and Weissman, Proc. Natl. Acad. Sci., 93:659-663, and U.S. Pat. Nos. 6,010,850 and 5,712,126; Welsh et al., Nucleic Acid Res., 20:4965-4970, 1992, and U.S. Pat. No. 5,487,985) and other RNA fingerprinting techniques, nucleic acid sequence based amplification ("NASBA") and other transcription based amplification systems (e.g., U.S. Pat. Nos. 5,409,818 and 5,554,527; WO 88/10315), polynucleotide arrays (e.g., U.S. Pat. Nos. 5,143,854, 5,424,186; 5,700,637, 5,874,219, and 6,054,270; PCT WO 92/10092; PCT WO 90/15070), Qbeta Replicase (PCT/US87/00880), Strand Displacement Amplification ("SDA"), Repair Chain Reaction ("RCR"), nuclease protection assays, subtraction-based methods, Rapid-Scan, etc. Additional useful methods include, but are not limited to, e.g., template-based amplification methods, competitive PCR (e.g., U.S. Pat. No. 5,747,251), redox-based assays (e.g., U.S. Pat. No. 5,871,918), Taqman-based assays (e.g., Holland et al., Proc. Natl. Acad, Sci., 88:7276-7280, 1991; U.S. Pat. Nos. 5,210,015 and 5,994,063), real-time fluorescence-based monitoring (e.g., U.S. Pat. No. 5,928,907), molecular energy transfer labels (e.g., U.S. Pat. Nos. 5,348,853, 5,532,129, 5,565,322, 6,030,787, and 6,117,635; Tyagi and Kramer, Nature Biotech., 14:303-309, 1996). Any method suitable for single cell analysis of gene or protein expression can be used, including in situ hybridization, immunocytochemistry, MACS, FACS, flow cytometry, etc. For single cell assays, expression products can be measured using antibodies, PCR, or other types of nucleic acid amplification (e.g., Brady et al., Methods Mol. & Cell. Biol. 2, 17-25, 1990; Eberwine et al., 1992, Proc. Natl. Acad. Sci., 89, 3010-3014, 1992; U.S. Pat. No. 5,723,290). These and other methods can be carried out conventionally, e.g., as described in the mentioned publications.

Activity of Flk-1, Trk-A, c-Met, and/or Bcr-Abl can be assessed routinely, e.g., as described in the examples below, or using standard assays for kinase activity.

Measuring expression includes evaluating the all aspects of the transcriptional and translational machinery of the gene. For instance, if a promoter defect causes, or is suspected of causing, the disorder, then a sample can be evaluated (i.e., "assessed") by looking (e.g., sequencing or restriction mapping) at the promoter sequence in the gene, by detecting transcription products (e.g., RNA), by detecting translation product (e.g., polypeptide). Any measure of whether the gene is functional can be used, including, polypeptide, polynucleotide, and functional assays for the gene's biological activity.

In making the assessment, it can be useful to compare the results to a gene which is not associated with the disorder, or to the same gene but in a unaffected tissue or region of the same tissue. The nature of the comparison can be determined routinely, depending upon how the assessing is accomplished. If, for example, the mRNA levels of a sample are detected, then the mRNA levels of a normal can serve as a comparison, or a gene which is known not to be affected by the disorder. Methods of detecting mRNA are well known, and discussed above, e.g., but not limited to, Northern blot analysis, polymerase chain reaction (PCR), reverse transcriptase PCR, RACE PCR, etc. Similarly, if polypeptide production is used to evaluate the gene, then the polypeptide in a normal tissue sample can be used as a comparison, or, polypeptide from a different gene whose expression is known not to be affected by the disorder. These are only examples of how such a method could be carried out.

Patients can also be selected for treatment if they have a particular genotype which is known to be associated with a cancer, especially genotypes associated with abnormal expression of Flk-1, Trk-A, and/or Bcr-Abl, including mutations in these genes. The present invention relates to methods for selecting patients for treatment involving determining the expression levels of Flk-1, Trk-A, and/or Bcr-Abl in a sample obtained from a subject, wherein abnormal levels of expression are associated with a disease, and administering a compound or composition of this invention to subjects who are identified as having said abnormal expression. The present invention relates to methods for selecting patients for treatment involving determining the presence of a Flk-1, Trk-A, and/or Bcr-Abl gene mutation in a sample obtained from a subject, wherein said mutation is associated with a disease, and administering a compound or composition of this invention to subjects who are identified as having said mutation.

The presence of the mutation can be determined conventionally, e.g., obtaining cells or a tissue sample from a subject, extracting nucleic acid from it, determining the gene sequence or structure of a target gene (using, e.g., mRNA, cDNA, genomic DNA, etc), comparing the sequence or structure of the target gene to the structure of the normal gene, whereby a difference in sequence or structure indicates a mutation in the gene in the subject. Mutations can be determined using any effective method, e.g., comparing restriction maps, nucleotide sequences, amino acid sequences, RFLPs, DNAse sites, DNA methylation fingerprints (e.g., U.S. Pat. No. 6,214,556), protein cleavage sites, molecular weights, electrophoretic mobilities, charges, ion mobility, etc., between a standard gene and the subject's gene. Proteins can also be compared. To carry out such methods, all or part of the gene or polypeptide can be compared. For example, if nucleotide sequencing is utilized, the entire gene can be sequenced, including promoter, introns, and exons, or only parts of it can be sequenced and compared, e.g., exon 1, exon 2, etc.

The present invention also provides methods of assessing the efficacy of a compound or composition of the present invention in treating a disease, comprising one or more of the following steps in any effective order, e.g., measuring the expression or activity of VEGFR-2, Trk-A, c-Met or Bcr-Abl in a sample obtained from said subject who has been treated with a compound of the present invention, and determining the effects of said compound on said expression or activity. The measuring step can be carried out as described already.

For instance, biopsy samples can be removed from patients who have been treated with a compound or composition of the present invention, and then assayed for the presence and/or activity of the mentioned signaling molecules. As discussed above, decreased levels of phospho-ERK in the cancer tissue (e.g., compared to a normal tissue or before treatment) indicate that the compound is exerting in vivo efficacy and a therapeutic effect.

Determining the effects of a compound or composition of this invention on expression or activity includes performing a comparison step between a tissue sample and a control, or other type of standard. Examples of standards that can be used, include, but are not limited to, a tissue sample prior to treatment, a tissue sample from an unaffected tissue or from an unaffected region of the affected tissue (e.g., from a region of the tissue which is not transformed, cancerous, etc.), etc. A standard can also be a value, or range of values, that is representative of normal levels of expression that have been established for that marker. The comparison can also be made between samples collected from at least two different timepoints during the treatment regimen with a compound of the present invention. For example, samples can be collected from various times after initiation of the drug treatment, and analysis of expression and/or activity levels can be used to monitor the progress/prognosis of the subject, e.g., how the subject is responding to the drug regimen. Any timepoint can be used, e.g., daily, twice a week, weekly, every two weeks, every month, yearly, a plurality of timepoints (at least 2, 3, 4, 8, 12, etc.).

The phrase "determining the effect" indicates that the result produced by a compound or composition is analyzed and/or identified. Any type of effect can be identified, e.g., where the expression and/or activity is reduced, decreased, down-regulated, inhibited, blocked, increased, up-regulated, unchanged, etc.

The method can be used to determine appropriate dosages and dosing regimens, e.g., how much compound or composition of this invention to administer and at what frequency to administer it. By monitoring its effect on the signaling molecules in the tissue, the clinician can determine the appropriate treatment protocol and whether it is achieving the desired effect, e.g., on modulating or inhibiting the signal transduction pathway. For instance, if a compound or composition of this invention is not effective in knocking down the amounts of a marker, e.g., Flk-1, Trk-A, c-Met, and/or Bcr-Abl, the dosage can be increased in the patient or given more frequently. Similarly, dosages and/or frequency can be reduced when it is shown that a compound or composition of this invention is effective in knocking down the levels of Flk-1, Trk-A, c-Met, and/or Bcr-Abl, or other marker for the disease state. Since a compound or composition of this invention can be administered in combination with others treatments, e.g., radiation, chemotherapy, and other agents, the monitoring of the subject can be used to assess the combined effects of the treatment regimen on the progress of the disease.

ABBREVIATIONS AND ACRONYMS

A comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meaning:

Abbreviations $^1$H NMR proton nuclear magnetic resonance
Ac acetyl
amu atomic mass unit
aq aqueous
Bu butyl
DMSO Dimethyl sulfoxide
ES Electrospray
Et ethyl
EtOAc Ethyl acetate
EtOH Ethanol
h hour(s)
HEPES N-(2-hydroxyethyl)-piperazine-N'-(2-ethane sulfonic acid)
HPLC High pressure liquid chromatography
LC-MS Liquid chromatography-coupled mass spectroscopy
M molar
m/z mass to charge ratio
S Me methyl
MeCN acetonitrile
MeOH methanol
mg milligram
MHz megahertz
min minute(s)
mL milliliter(s)
mmol millimole(s)
mol mole(s)
mp melting point
NMR Nuclear magnetic resonance
Ph phenyl
ppm parts per million
Pr propyl
THF Tetrahydrofuran The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated under reduced pressure" or "solvent was removed under reduced pressure" usually refers to the use of a Buchi rotary evaporator at approximately 15 mm of Hg. In some cases, a centrifugal multiple sample evaporator (e.g., GeneVac Atlas) was used for the removal of solvent under reduced pressure. All temperatures are reported uncorrected in degrees Celsius (° C.). Thin layer chromatography (TLC) was performed on pre-coated glass-backed silica gel 60 A F-254 250 μm plates Electron impact mass spectra (EI-MS) were obtained with a Hewlett Packard 5989A mass spectrometer equipped with a Hewlett Packard 5890 Gas Chromatograph with a J & W DB-5 column (0.25 μM coating; 30 m×0.25 mm). The ion source was maintained at 250° C. and spectra were scanned from 50-800 amu at 2 sec per scan.

LC-MS: High pressure liquid chromatography-electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2×23 mm, 120 A), and a Micromass LCZ single quadrupole mass spectrometer with z-spray electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in acetonitrile with 0.02% TFA at 1.5 mL/min. Samples were eluted as follows: 90% A for 0.5 minutes ramped to 95% B over 3.5 minutes and held at 95% B for 0.5 minutes, and then the column was brought back to initial conditions over 0.1 minutes. Total run time was 4.8 minutes.

NMR: Routine one-dimensional NMR spectroscopy was performed on 300/400 MHz Varian Mercury-plus spectrometers. The samples were dissolved in deuterated solvents obtained from Cambridge Isotope Labs, and transferred to 5 mm ID Wilmad NMR tubes. The spectra were acquired at 293 K. The chemical shifts were recorded on the ppm scale and were referenced to the appropriate solvent signals, such as 2.05 ppm for acetone-$d_6$, 2.49 ppm for DMSO-$d_6$, 1.93 ppm for $CD_3CN$, 3.30 ppm for $CD_3OD$, 5.32 ppm for $CD_2Cl_2$ and 7.26 ppm for $CDCl_3$ for $^1$H spectra. Abbreviations: br, broad; s, singlet; d, doublet; dd, doublet of doublets; ddd, doublet of doublet of doublets; t, triplet; q, quartet; m, multiplet.

Preparative HPLC: Preparative HPLC was carried out in reversed phase mode, eluting with aqueous acetonitrile containing 0.5% TFA, typically using a Gilson HPLC system equipped with two Gilson 322 pumps, a Gilson 215 Autosampler, a Gilson diode array detector, and a YMC Pro C-18 column (20×150 mm, 120 A). Gradient elution was used with Buffer A as water with 0.1% TFA and Buffer B as acetonitrile with 0.1% TFA. Sample was dissolved in MeOH or MeOH/DMSO with concentration about 50 mg/mL. Injection volume was about 2-3 mL/injection. Sample was typically eluted as follows: 10-90% B over 15 minutes with flow rate of 25 mL/min, hold 2 minutes, back to 10% B. The desired fraction(s) were collected by UV monitoring at 254 or 220 nm and evaporated under reduced pressure by using a GeneVac centrifugal multiple sample evaporator.

By using the methods described herein, the compounds of the invention may be prepared. The following specific examples are presented to illustrate the invention described herein, but they should not be construed as limiting the scope of the invention in any way.

EXAMPLE 1
HYDROXY METHYL PHENYL PYRAZOLYL UREA (4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide)
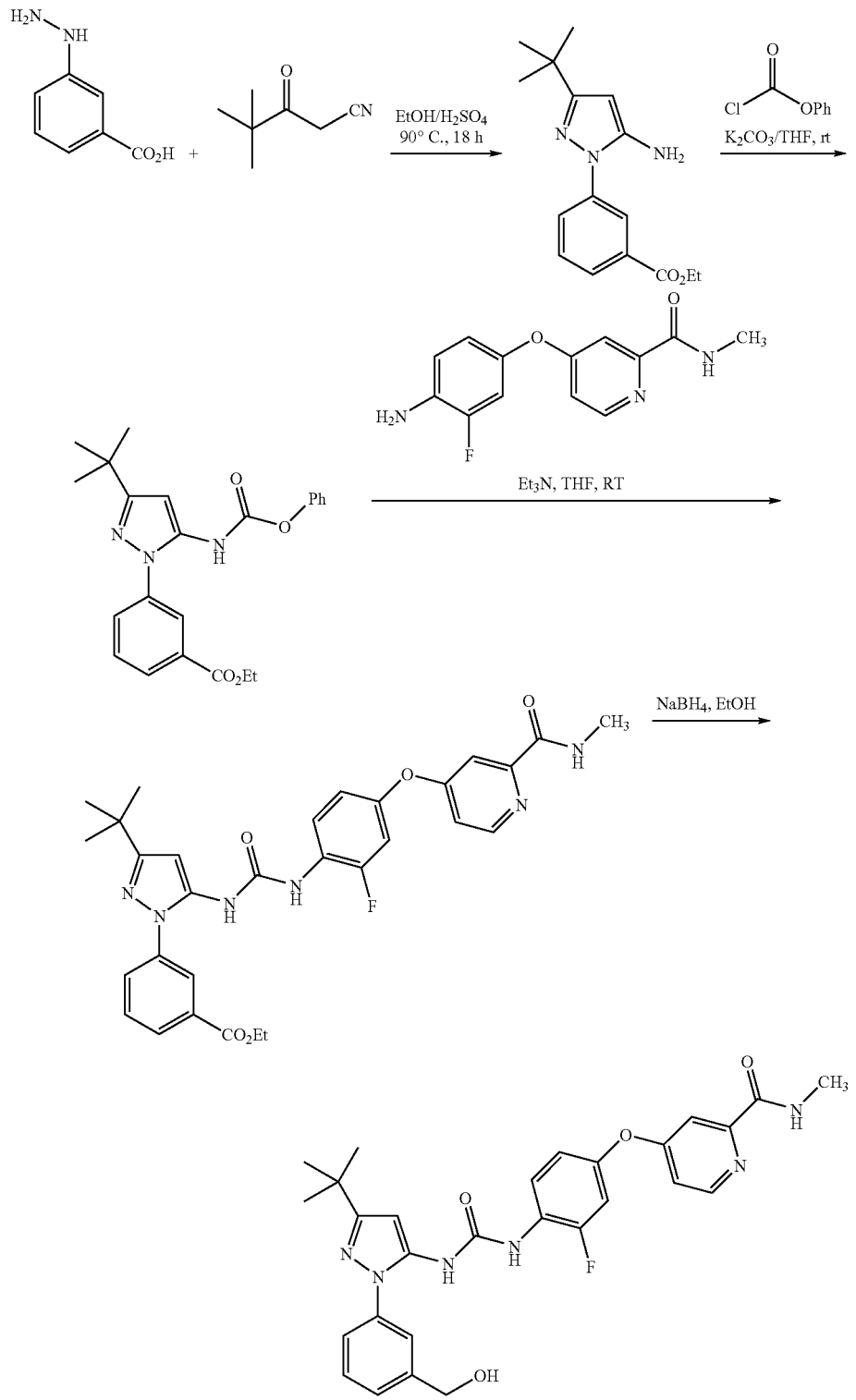

Step 1. Preparation of ethyl 3-(5-amino-3-tert-butyl-1H-pyrazol-1-yl)benzoate

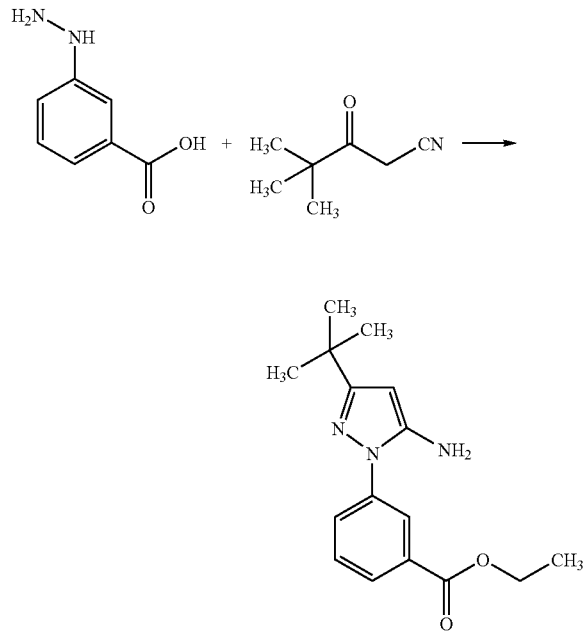

Sulfuric acid (concentrated, 15.7 mL, 295.7 mmol) was carefully added drop-wise to cold EtOH (600 mL) with stirring. To this, 3-hydrazinobenzoic acid (45 g, 295.7 mmol) and 4,4-dimethyl-3-oxopentanenitrile (40.7 g, 325.3 mmol) were added and then the mixture was heated at 90° C. for 48 h. Most of the solvent was evaporated at reduced pressure, and the residual mixture was diluted with ethyl acetate. The resulting mixture was washed with ice cold 2M NaOH followed by brine, and dried (Na$_2$SO$_4$). The solution was filtered through a bed of silica gel, washing with more ethyl acetate. Evaporation of ethyl acetate and treatment of the residue with dichloromethane/hexanes gave the product as an off-white crystalline solid (61 g, 71%). MS m/z 288.2 (M+H)$^+$; calcd. mass 287. Retention time (LC-MS): 2.99 min. $^1$H-NMR (DMSO-d$_6$): δ 8.16 (m 1H); 7.88 (m, 2H); 7.60 (t, 1H); 5.40 (s, 1H); 5.32 (s, 2H); 4.36 (q, 2H); 1.34 (t, 3H); 1.21 (s, 9H).

Step 2. Preparation of ethyl 3-{3-tert-butyl-5-[(phenoxycarbonyl)amino]-1H-pyrazol-1-yl}benzoate

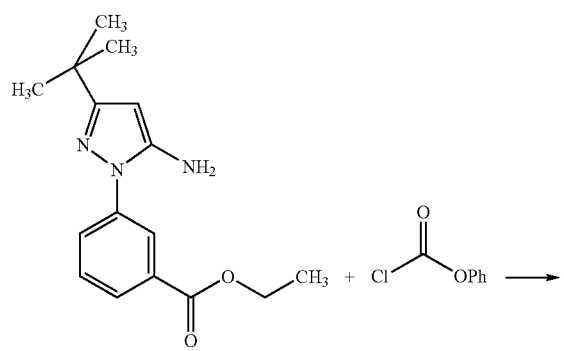

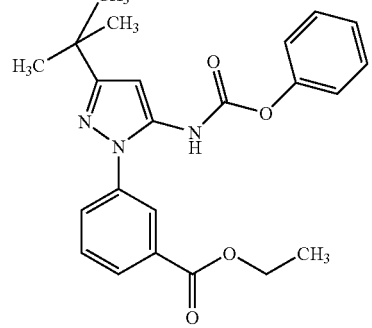

To a mixture of ethyl 3-(5-amino-3-tert-butyl-1H-pyrazol-1-yl)benzoate (60 g, 208.8 mmol) and K$_2$CO$_3$ (86.6 g, 626.4 mmol) in THF (1400 mL) was added phenyl chloroformate (98.1 g, 626.4 mmol). The reaction was stirred at room temperature overnight. The solid was removed by filtration and most of the solvent was evaporated under reduced pressure. The residual mixture was dissolved in EtOAc and washed with brine, then water. The organic layer was then dried and concentrated. The crude product was purified by recrystallization from CH$_2$Cl$_2$/hexanes to give the desired product as a white powder (78.5 g, 92%). MS m/z 408.1 (M+H)$^+$; calcd. mass 407. Retention time (LC-MS): 3.92 min. $^1$H-NMR (DMSO-d$_6$): δ 10.19 (s, broad, 1H); 8.11 (m 1H); 7.97 (d, J=7.6 Hz, 1H); 7.86 (m, 1H); 7.71 (t, 1H); 7.38 (m, 2H); 7.24 (m, 1H); 7.08 (m, 1H); 6.40 (s, 1H); 4.38 (q, 2H); 1.32 (t, 3H); 1.29 (s, 9H).

Step 3. Preparation of ethyl 3-(3-tert-butyl-5-{[(2-fluoro-4-{[2-(methylcarbamoyl)-pyridin-4-yl]oxy}phenyl)carbamoyl]amino}-1H-pyrazol-1-yl)benzoate

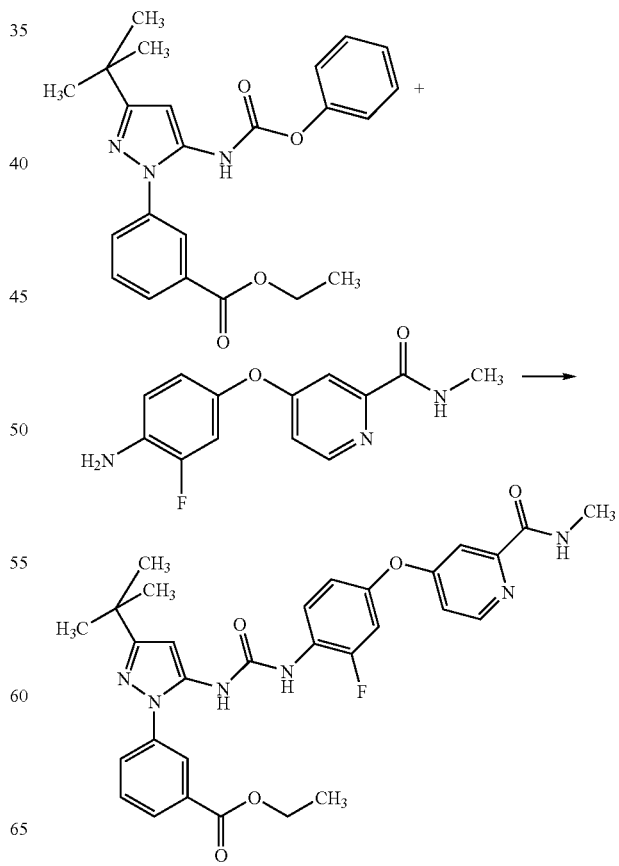

A solution of ethyl 3-{3-tert-butyl-5-[(phenoxycarbonyl)amino]-1H-pyrazol-1-yl}benzoate (9.36 g, 22.0 mmol), 4-(4-amino-3-fluorophenoxy)-N-methylpyridine-2-carboxamide (5.0 g, 19.1 mmol; prepared as described in Dumas et al., PCT Int. Appl. WO 2004078748 (2004)) and triethyl amine (3.87 g, 38.3 mmol) in anhydrous THF (100 mL) was stirred at room temperature overnight. The crude product was purified by column chromatography (CH$_2$Cl$_2$ plus 1% to 3% of 2M NH$_3$ in MeOH), followed by recrystallization from EtOAc/hexanes to give the desired product as an off-white crystalline solid (6.32 g, 57%). MS m/z 575.1 (M+H)$^+$; calcd. mass 574. Retention time (LC-MS): 3.75 min. $^1$H-NMR (DMSO-d$_6$): δ 8.97 (m, 1H); 8.89 (m, 1H); 8.80 (m, 1H); 8.52 (d, J=5.6 Hz, 1H); 8.16 (t, 1H); 8.06 (m, 1H); 7.99 (m, 1H); 7.85 (m, 1H); 7.71 (t, 1H); 7.39 (m, 1H); 7.33 (m, 1H); 7.17 (m, 1H); 7.06 (m, 1H); 6.42 (s, 1H); 4.36 (q, 2H); 2.78 (d, J=5.2 Hz, 3H); 1.31 (m, 12H).

Step 4. Preparation of (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide)

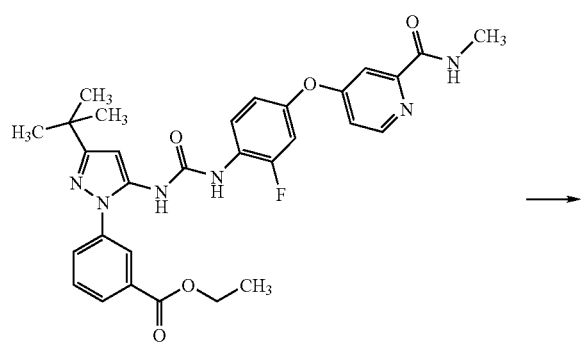

To a well-stirred cooled solution of 4-(4-{3-[5-tert-butyl-2-(3-ethoxycarbonyl-phenyl)-2H-pyrazol-3-yl]-ureido}-3-fluoro-phenoxy)-pyridine-2-carboxylic acid methylamide (56 mg, 0.1 mmol) in ethanol (10 mL), NaBH$_4$ (50 mg) was added in portions. After 14 h, ice water (10 mL) was carefully added to the reaction mixture. Then, most of the ethanol was evaporated under reduced pressure. The residual mixture was treated with saturated aqueous ammonium chloride solution (10 mL) and extracted three times with dichloromethane (50, 25, and 25 mL). The combined dichloromethane extract was dried (sodium sulfate) and the solvent was evaporated. The crude product was purified by preparative thin layer chromatography on silica gel using 3-5% 2M ammonia in methanol in dichloromethane as the eluent to yield the desired product as a white powder (31 mg, 58%).

For a larger scale synthesis, the following similar procedure was followed: To a solution of ethyl 3-(3-tert-butyl-5-{[(2-fluoro-4-{[2-(methylcarbamoyl)pyridin-4-yl]oxy}-phenyl)carbamoyl]amino}-1H-pyrazol-1-yl)benzoate (11.2 g, 19.5 mmol) in EtOH was added NaBH$_4$ stepwise as a solid. The reaction was then stirred at room temperature overnight, and then quenched by gradual addition of aqueous NH$_4$Cl. The mixture was diluted with EtOAc, washed with aq. NH$_4$Cl, followed by brine. The organic layer was then dried and concentrated. The crude product was then purified by column chromatography on silica gel (CH$_2$Cl$_2$ plus 1 to 5% of 2M NH$_3$ in MeOH), followed by recrystallization from dichloromethane/hexanes to give the desired product as a white crystalline solid (8.0 g, 77%). Mp 160° C.; after further recrystallization, desired product was obtained with mp 196° C. MS m/z 533.3 (M+H)$^+$; calcd. mass 532. Retention time (LC-MS): 3.13 min. $^1$H-NMR (DMSO-d$_6$): δ 9.02 (s, broad, 1H); 8.87 (s, 1H); 8.81 (m, 1H); 8.52 (d, J=5.2 Hz, 1H); 8.21 (t, 1H); 7.51 (m, 2H); 7.39 (m, 3H); 7.32 (m, 1H); 7.17 (m, 1H); 7.06 (m, 1H); 6.40 (s, 1H); 5.36 (t, 1H); 4.59 (d, J=5.6 Hz, 2H); 2.78 (d, J=4.8 Hz, 3H); 1.27 (s, 9H). Elemental Analysis: C, 62.92%; H, 5.43%; N, 15.70%; calcd. C, 63.15%; H, 5.49%; N, 15.78%.

EXAMPLE 2

4-{4-[({3-tert-Butyl-1-[3-(hydroxymethyl)phenyl]-1H-pyrazol-5-yl}carbamoyl)-amino]-3-fluorophenoxy}-N-methylpyridine-2-carboxamide, bis(4-methyl-benzenesulfonate) salt

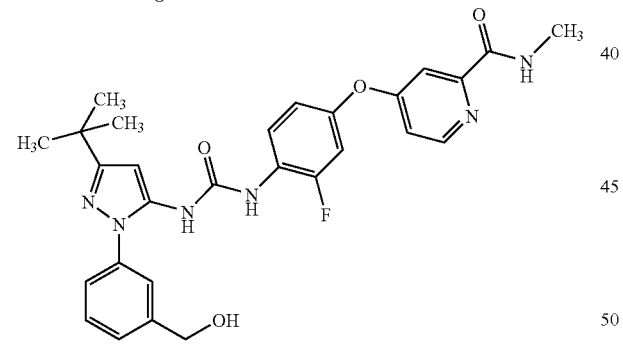

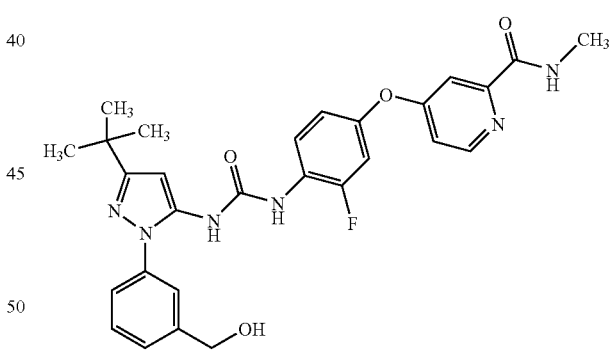

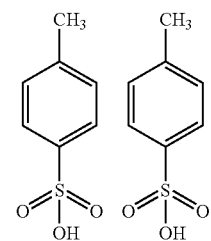

To a solution of (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, 200 mg, 0.376 mmol) in 1,4-dioxane (5 mL) was dropwise added 4-toluenesulfonic acid monohydrate (143 mg, 0.75 mmol). The precipitate formed was filtered and washed with dioxane, followed by hexanes. The solid was the recrystallized from dioxane/methanol to give the desired product salt as a crystalline white powder (115.8 mg, 35%). Mp 184° C. MS m/z 533.2 (M+H)$^+$; calcd. mass 532. Retention time (LC-MS): 3.48 min. $^1$H-NMR (DMSO-d$_6$): δ 9.04 (s, broad, 1H); 8.88 (s, 1H); 8.87 (m, 1H); 8.54 (d, J=5.6 Hz, 1H); 8.22 (t, 1H); 7.51 (m, 7H); 7.38 (m, 2H); 7.34 (m, 1H); 7.21 (m, 1H); 7.11 (d, J=7.6 Hz, 4H); 7.07 (m, 1H); 6.40 (s, 1H); 4.58 (s, 2H); 2.79 (d, J=4.8 Hz, 3H); 2.28 (s, 6H); 1.27 (s, 9H).

EXAMPLE 3

4-{4-[({3-tert-Butyl-1-[3-(hydroxymethyl)phenyl]-1H-pyrazol-5-yl}carbamoyl)-amino]-3-fluorophenoxy}-N-methylpyridine-2-carboxamide, dimethanesulfonate salt

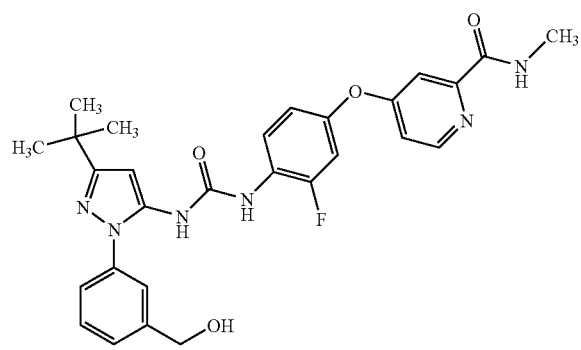

To a solution of (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, 225 mg, 0.42 mmol) in 1,4-dioxane (5 mL) was dropwise added 4-methanesulfonic acid (81 mg, 0.84 mmol). The precipitate that formed was filtered and washed with dioxane, followed by hexanes. The solid was then recrystallized from acetone/methanol to give the desired product salt as a crystalline white powder (156.7 mg, 51%). Mp 158° C. MS m/z 533.1 (M+H)$^+$; calcd. mass 532. Retention time (LC-MS): 3.21 min. $^1$H-NMR (DMSO-d$_6$): δ 9.04 (s, broad, 1H); 8.88 (s, 1H); 8.87 (m, 1H); 8.54 (d, J=6 Hz, 1H); 8.22 (t, 1H); 7.51 (m, 3H); 7.38 (m, 2H); 7.33 (m, 1H); 7.21 (m, 1H); 7.06 (m, 1H); 6.40 (s, 1H); 4.58 (s, 2H); 2.79 (d, J=5.2 Hz, 3H); 2.35 (s, 6H); 1.27 (s, 9H).

EXAMPLE 4

4-{4-[({3-tert-Butyl-1-[3-(hydroxymethyl)phenyl]-1H-pyrazol-5-yl}carbamoyl)-amino]-3-fluorophenoxy}-N-methylpyridine-2-carboxamide, dihydrochloride salt

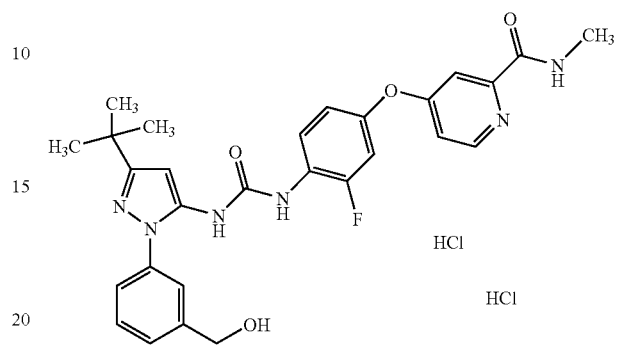

To a solution of (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, 220 mg, 0.41 mmol) in 1,4-dioxane (10 mL) was dropwise added hydrochloric acid (30 mg, 0.82 mmol). The precipitate that formed was filtered and washed with dioxane, followed by hexanes. The solid was then recrystallized from dioxane/methanol to give the desired product salt as a white powder (240 mg, 95%). MS m/z 533.3 (M+H)$^+$; calcd. mass 532. Retention time (LC-MS): 3.13 min. $^1$H-NMR (DMSO-d$_6$): δ 9.10 (s, broad, 1H); 8.97 (s, 1H); 8.87 (m, 1H); 8.53 (d, J=5.6 Hz, 1H); 8.21 (t, 1H); 7.50 (m, 3H); 7.39 (m, 2H); 7.33 (m, 1H); 7.20 (m, 1H); 7.06 (m, 1H); 6.39 (s, 1H); 4.58 (s, 2H); 2.79 (d, J=4.8 Hz, 3H); 1.27 (s, 9H).

EXAMPLE 5

4-{4-[({3-tert-Butyl-1-[3-(hydroxymethyl)phenyl]-1H-pyrazol-5-yl}carbamoyl)-amino]-3-fluorophenoxy}-N-methylpyridine-2-carboxamide, bis(benzene-sulfonate) salt

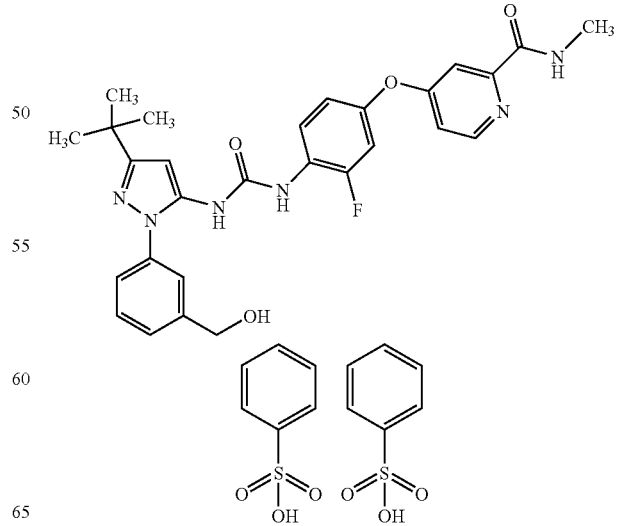

To a solution of (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, 212 mg, 0.40 mmol) in acetone (5 mL) was dropwise added benzenesulfonic acid (157 mg, 1.0 mmol). The precipitate that formed was filtered and washed with acetone, followed by hexanes to give the desired product salt as a crystalline white powder (271.4 mg, 80%). MS m/z 533.5 (M+H)+; calcd. mass 532. Retention time (LC-MS): 3.15 min. $^1$H-NMR (DMSO-$d_6$): δ 9.05 (s, broad, 1H); 8.88 (m, 2H); 8.54 (d, J=6.0 Hz, 1H); 8.22 (t, 1H); 7.59 (m, 4H); 7.51 (m, 3H); 7.38 (m, 2H); 7.34 (m, 7H); 7.22 (m, 1H); 7.07 (m, 1H); 6.41 (s, 1H); 4.58 (s, 2H); 2.79 (d, J=4.8 Hz, 3H); 1.27 (s, 9H).

EXAMPLE 6

4-{4-[({3-tert-Butyl-1-[3-(hydroxymethyl)phenyl]-1H-pyrazol-5-yl}carbamoyl)-amino]-3-fluorophenoxy}-N-methylpyridine-2-carboxamide, dihydrogen bromide salt

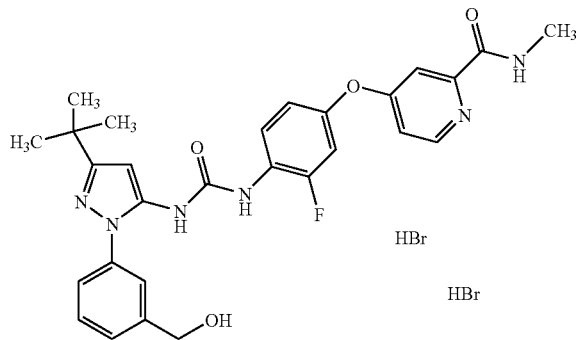

To a solution of (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, 400 mg, 0.751 mmol) in acetone (5 mL) was dropwise added a solution of 48% HBr (1 mL) in water. The precipitate that formed was filtered and washed with acetone, followed by hexanes to give the desired product salt as a white powder (505 mg, 96.8%). MS m/z 533.4 (M+H)+; calcd. mass 532. Retention time (LC-MS): 3.36 min. $^1$H-NMR (DMSO-$d_6$): δ 9.03 (s, broad, 1H); 8.89 (m, 2H); 8.53 (d, J=5.6 Hz, 1H); 8.21 (m, 1H); 7.50 (m, 3H); 7.37 (m, 2H); 7.33 (m, 1H); 7.20 (m, 1H); 7.06 (m, 1H); 6.40 (s, 1H); 4.58 (s, 2H); 2.78 (m, 3H); 1.26 (s, 9H).

EXAMPLE 7

4-{4-[({3-tert-Butyl-1-[3-(hydroxymethyl)phenyl]-1H-pyrazol-5-yl}carbamoyl)-amino]-3-fluorophenoxy}-N-methylpyridine-2-carboxamide, hydrogen sulfate salt

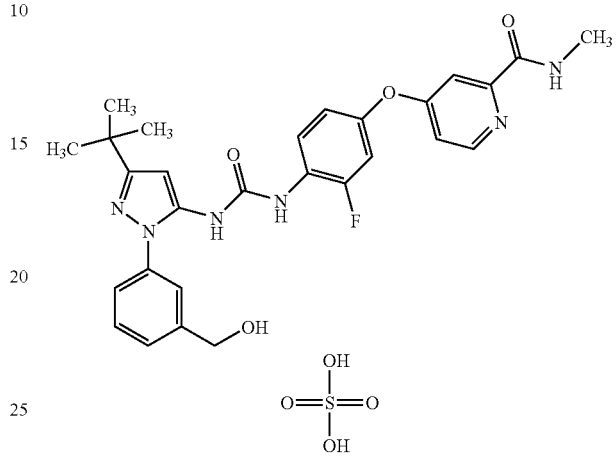

To a solution of (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, 400 mg, 0.751 mmol) in acetone (5 mL) was dropwise added a solution of sulfuric acid (500 mg, 5.1 mmol) in ethyl acetate (5 mL) The precipitate that formed was filtered and washed with acetone, followed by hexane to give the desired product salt as a crystalline white powder (460 mg, 97%). MS m/z 533.4 (M+H)+; calcd. mass 532. Retention time (LC-MS): 3.20 min. $^1$H-NMR (DMSO-$d_6$): δ 9.02 (m, 1H); 8.88 (m, 2H); 8.52 (d, J=6.0 Hz, 1H); 8.22 (m, 1H); 7.50 (m, 2H); 7.42 (m, 1H); 7.37 (m, 2H); 7.32 (m, 1H); 7.19 (m, 1H); 7.05 (m, 1H); 6.39 (s, 1H); 4.57 (s, 2H); 2.78 (m, 3H); 1.26 (s, 9H).

EXAMPLE 8

3-(3-tert-Butyl-5-{[(2-fluoro-4-{[2-(methylcarbamoyl)pyridin-4-yl]oxy}phenyl)carbamoyl]amino}-1H-pyrazol-1-yl)benzyl-N-[(9H-fluoren-9-ylmethoxy)carbonyl]D valinate

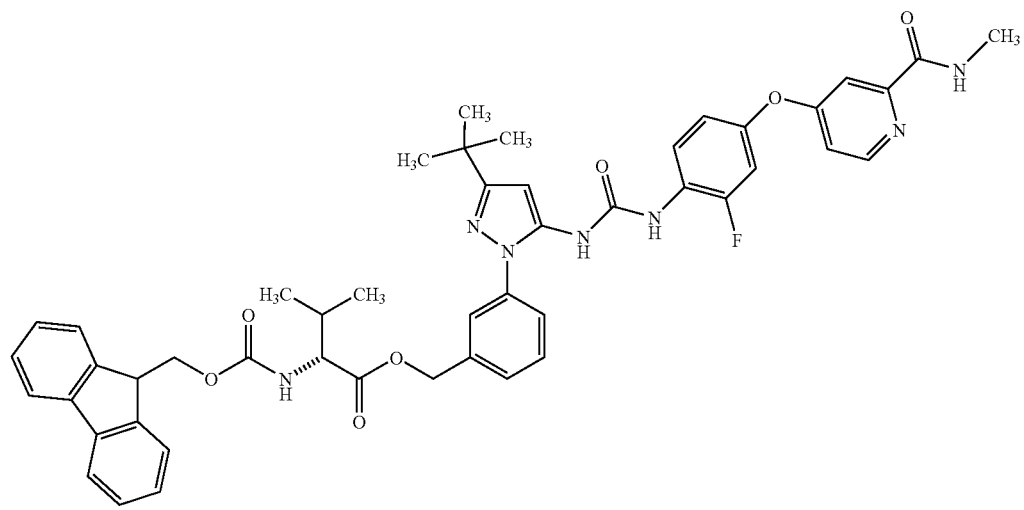

To a room temperature solution of example 1, (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, (1.00 g, 1.88 mmol) and potassium carbonate (1.30 g, 9.39 mmol) in tetrahydrofuran (40 mL) was added N-(9-fluoroenylmethyloxycarbonyl)-D-Valine-chloride (Fmoc-D-Val-Cl), (1.34 g, 3.76 mmol). The reaction mixture was allowed to stir overnight. The crude material was concentrated and purified via column chromatography (CH$_2$Cl$_2$: 2M NH$_3$ in MeOH, 99:1 up to 97:3) to afford 1.20 g (75%) of the desired product as a white powder. MS m/z 854.4 (M+H)$^+$; Retention time (LC-MS): 4.59 min.

EXAMPLE 9

3-(3-tert-Butyl-5-{[(2-fluoro-4-{[2-(methylcarbamoyl)pyridin-4-yl]oxy}phenyl)-carbamoyl]amino}-1H-pyrazol-1-yl)benzyl D-valinate

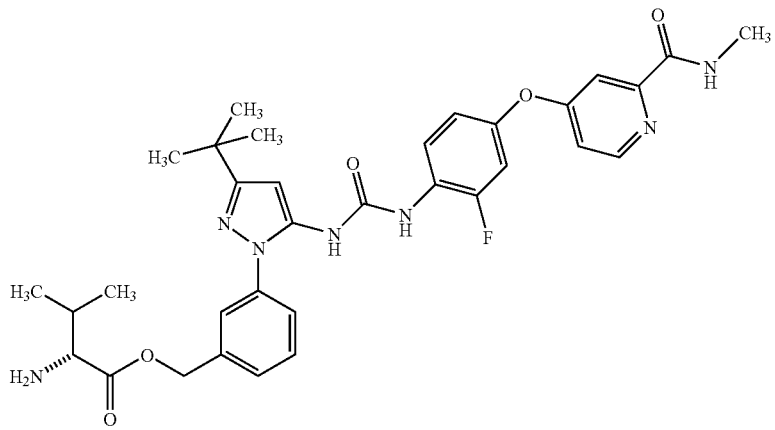

A solution of example 8,3-(3-tert-butyl-5-[(2-fluoro-4-[2-(methylcarbamoyl)pyridin-4-yl]oxyphenyl)-carbamoyl]amino-1H-pyrazol-1-yl)benzyl-N-[(9H-fluoren-9-yl-methoxy)-carbonyl]-valinate, (1.10 g, 1.29 mmol) in piperidine (0.16 mL)/DMF (9.17 mL) was allowed to stir at room temperature for 20 min. The reaction mixture was diluted with EtOAc (20 mL) and washed with water (3×). The combined organic layer was dried and concentrated. The crude material was purified via prep-TLC (CH$_2$Cl$_2$:2M NH$_3$ in MeOH, 97:3) to afford 0.48 g (59%) of the desired product as a white powder. MS m/z 632.2 (M+H)$^+$; Retention time (LC-MS): 2.73 min.

EXAMPLE 10

3-(3-tert-Butyl-5-{[(2-fluoro-4-{[2-(methylcarbamoyl)pyridin-4-yl]oxy}-phenyl)carbamoyl]amino}-1H-pyrazol-1-yl)benzyl L-valinate

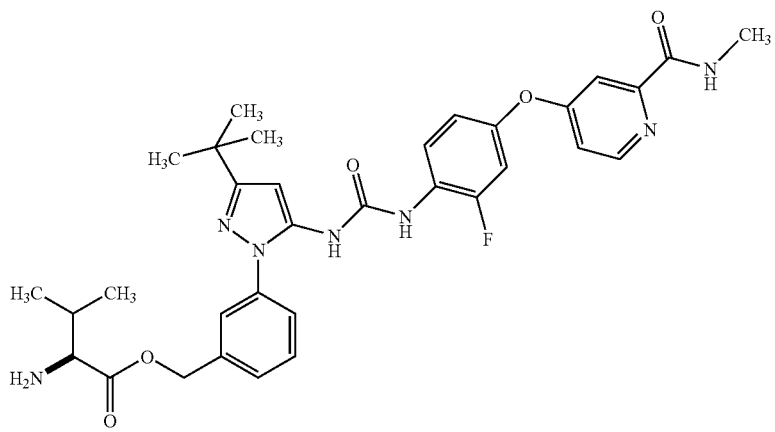

Step 1: To a 0° C. solution of Example 1, (4-{4-[({3-tert-butyl-1-[3-(hydroxyl-methyl)phenyl]-1H-pyrazol-5-yl}carbamoyl)amino]-3-fluorophenoxy}-N-methyl-pyridine-2-carboxamide (0.200 g, 0.38 mmol), 1-hydroxybenzotriazole (0.05 g, 0.38 mmol), and Fmoc-L-Val-Cl (0.13 g, 0.38 mmol) in chloroform (6 mL) was added 1-(3-dimethylaminopropyl)-3-ethlycarboxiimide hydrochloride (0.11 g, 0.56 mmol). The reaction mixture was allowed to warm to room temperature and stir for 72 h. The crude material was concentrated and purified via prep-TLC (CH$_2$Cl$_2$:2M NH$_3$ in MeOH, 97:3) to afford 0.24 g (74%) of 3-(3-tert-butyl-5-[(2-fluoro-4-[2-(methylcarbamoyl)pyridin-4-yl]oxy-phenyl)-carbamoyl]amino-1H-pyrazol-1-yl)benzyl-N-[(9H-fluoren-9-ylmethoxy)-carbonyl]-L-valinate as a white powder. MS m/z 854.3 (M+H)$^+$; Retention time (LC-MS): 4.08 min.

Step 2: A solution of 3-(3-tert-butyl-5-[(2-fluoro-4-[2-(methylcarbamoyl)pyridin-4-yl]oxyphenyl)-carbamoyl]amino-1H-pyrazol-1-yl)benzyl-N-[(9H-fluoren-9-ylmethoxy)-carbonyl]-L-valinate (0.20 g, 0.23 mmol) in piperidine (0.26 mL)/DMF (15 mL) was allowed to stir at room temperature for 20 min. The reaction mixture was diluted with EtOAc (20 mL) and washed with water (3×). The combined organic layer was dried and concentrated. The crude material was purified via prep-TLC (CH$_2$Cl$_2$:2M NH$_3$ in MeOH, 97:3) to afford 0.11 g (76%) of the desired product as a white powder. MS m/z 632.2 (M+H)$^+$; Retention time (LC-MS): 3.11 min.

EXAMPLE 11

3-(3-tert-Butyl-5-{[(2-fluoro-4-{[2-(methylcarbamoyl)pyridin-4-yl]oxy}-phenyl)carbamoyl]amino}-1H-pyrazol-1-yl)benzyl acetate

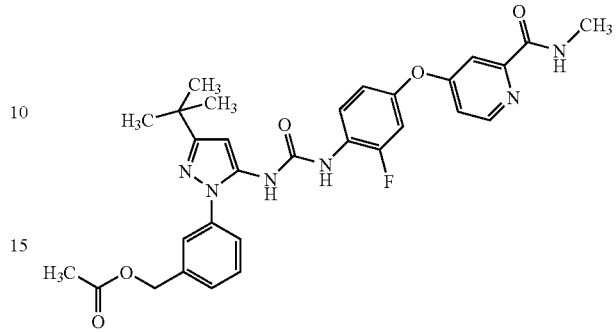

To a 0° C. solution of example 1, (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, (1.00 g, 1.88 mmol) in dichloromethane (15 mL) was added dropwise acetyl chloride (0.15 mL, 2.07 mmol). The reaction mixture was allowed to stir at 0° C. for 1 h. The reaction mixture was quenched with water and extracted with CH$_2$Cl$_2$. The combined organic layer was dried and concentrated. The crude material was purified via column chromatography (CH$_2$Cl$_2$:2M NH$_3$ in MeOH, 97:3) to afford 0.32 g (30%) of the desired product as a white powder. MS m/z 575.1 (M+H)$^+$; Retention time (LC-MS): 3.55 min.

EXAMPLE 12

Di-tert-butyl 3-(3-tert-butyl-5-{[(2-fluoro-4-{[2-(methylcarbamoyl)pyridin-4-yl]oxy}phenyl)carbamoyl]amino}-1H-pyrazol-1-yl)benzyl phosphate

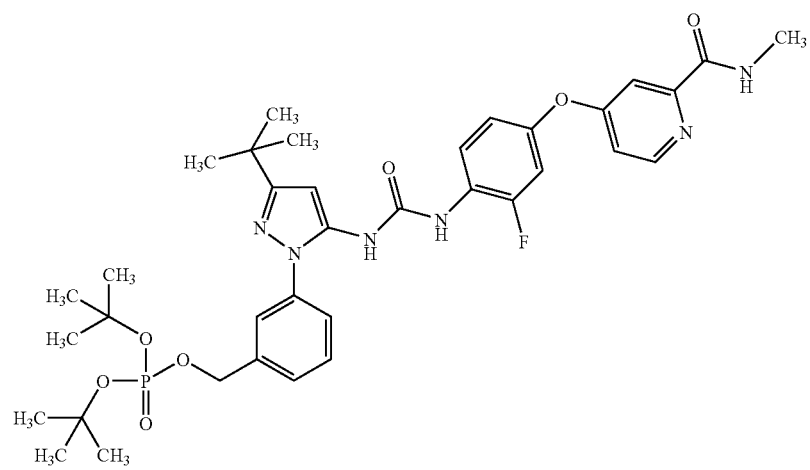

To a room temperature solution of 1-H-tetrazole (0.45M in acetonitrile, 56 mL, 25.3 mmol, solvent removed in vacuo prior to using) in tetrahydrofuran (100 mL) was added example 1, (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, (5.00 g, 9.39 mmol) and di-t-butyl N,N-diethylphosphoramidite (2.11 g, 8.45 mmol). The reaction mixture was allowed to stir at room temperature for 2 h. The reaction mixture was then cooled to −40° C. and a slurry of m-chloroperoxybenzoic acid (85% in CH$_2$Cl$_2$, 2.74 g, 12.2 mmol) was added while keeping the reaction temperature below 0° C. The reaction mixture was allowed to warm to room temperature and stir for 10 min and then an aqueous solution of NaHSO$_3$ (10%, 40 mL) was added. After stirring for an additional 1 h at room temperature, the reaction was transferred to a separatory funnel and extracted with EtOAc. The organic layer was washed with NaHCO$_3$ (2×50 mL), dried (NaSO$_4$) and concentrated. The crude material was purified via column chromatography (CH$_2$Cl$_2$:2 M NH$_3$ in MeOH, 98:2), followed by recrystallization (CH$_2$Cl$_2$/hexanes) to afford 3.57 g (52%) of the desired product as a white crystalline material. MS m/z 724.9 (M+H)$^+$; Retention time (LC-MS): 3.74 min.

EXAMPLE 13

3-(3-tert-Butyl-5-{[(2-fluoro-4-{[2-(methylcarbamoyl)pyridin-4-yl]oxy}-phenyl)carbamoyl]amino}-1H-pyrazol-1-yl)benzyl dihydrogen phosphate dihydrochloride

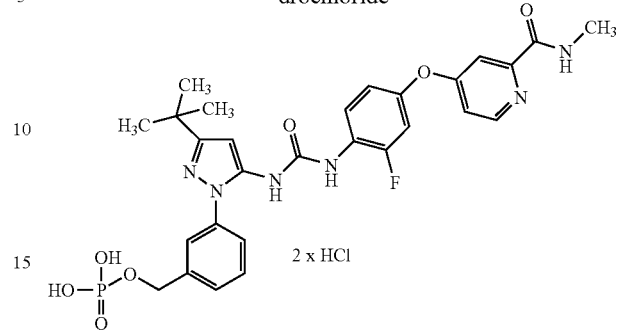

To a room temperature solution of example 12, di-tert-butyl 3-(3-tert-butyl-5-{[(2-fluoro-4-{[2-(methylcarbamoyl)pyridin-4-yl]oxy}phenyl)carbamoyl]amino}-1H-pyrazol-1-yl)benzyl phosphate, (0.45 g, 0.62 mmol) in dioxane (12 mL) was slowly added HCl/dioxane (4M, 4 mL, 16 mmol). A white precipitate formed and the suspension was stirred at room temperature for 3 h. The reaction mixture was diluted with ether (20 mL) and the solids were collected. The resulting solids were washed with ether followed by hexanes to afford 0.40 g (94%) of the desired product as a white powder. MS m/z 612.9 (M+H)$^+$; Retention time (LC-MS): 3.05 min.

EXAMPLE 14

4-{[3-(3-tert-Butyl-5-{[(2-fluoro-4-{[2-(methylcarbamoyl)pyridin-4-yl]oxy}-phenyl)carbamoyl]amino}-1H-pyrazol-1-yl)benzyl]oxy}-4-oxobutanoic acid

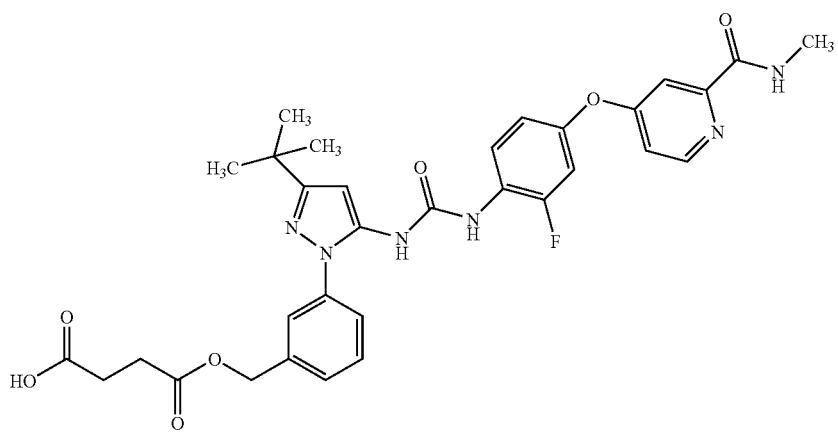

To a room temperature solution of example 1, (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, (0.45 g, 0.85 mmol) in tetrahydrofuran (43 mL) was added succinic anhydride (0.10 g, 1.00 mmol). The reaction mixture was allowed at stir at room temperature for 72 h. The reaction mixture was concentrated and the residue was triturated with hexanes. The resulting white powder was filtered and washed with hexanes. The solids were re-dissolved in EtOAc, washed with sat. aqueous ammonium chloride solution (2×15 mL), dried (NaSO$_4$) and concentrated to afford 0.49 g (91%) of pure product. MS m/z 633.1 (M+H)$^+$; Retention time (LC-MS): 3.29 min.

EXAMPLE 15

3-(3-tert-Butyl-5-{[(2-fluoro-4-{[2-(methylcarbamoyl)pyridin-4-yl]oxy}phenyl)carbamoyl]amino}-1H-pyrazol-1-yl)benzyl methoxyacetate

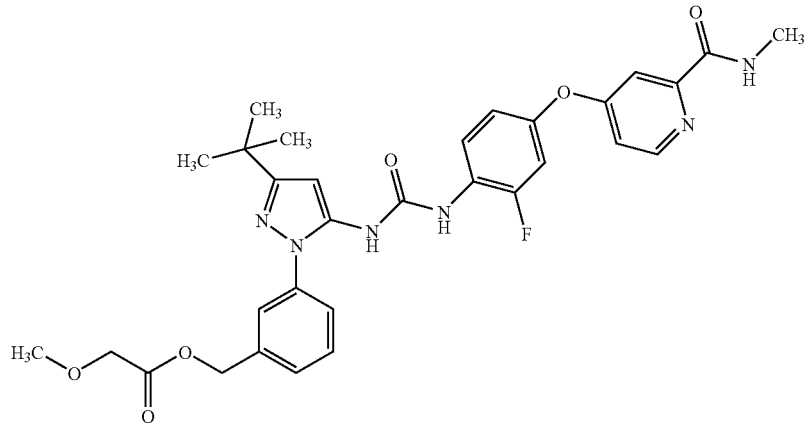

To a 0° C. solution of example 1, (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, (0.15 g, 0.28 mmol) in dichloromethane (1.5 mL)/pyridine (0.5 mL) was added dropwise methoxyacetyl chloride (0.03 mL, 0.34 mmol). The reaction mixture was allowed to warm to room temperature and stir for 72 h. The reaction mixture was diluted with EtOAc and washed with sat. aqueous.NaHCO$_3$. The combined organic layer was washed with brine, dried and concentrated. The crude material was purified via column chromatography (CH$_2$Cl$_2$: MeOH, 100% CH$_2$Cl$_2$ to 98.5:1.5) to afford 0.16 g (96%) of the desired product as a white solid. MS m/z 605.1 (M+H)$^+$; Retention time (LC-MS): 3.44 min.

EXAMPLE 16

3-(3-tert-butyl-5-{[(2-fluoro-4-{[2-(methylcarbamoyl)pyridin-4-yl]oxy}phenyl)carbamoyl]amino}-1H-pyrazol-1-yl)benzyl propionate

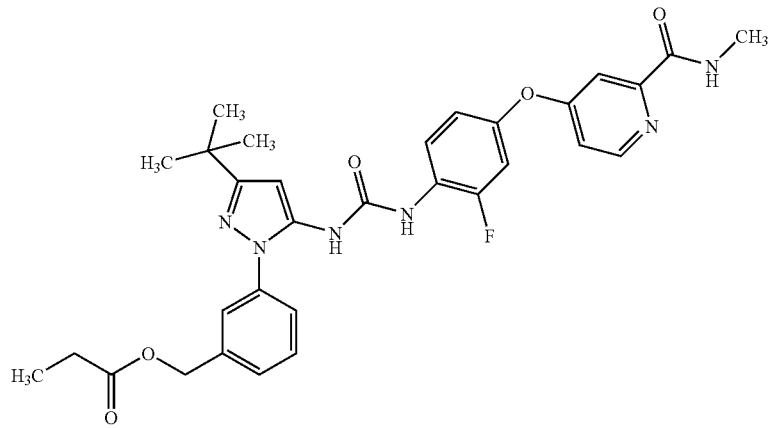

To a room temperature solution of example 1, (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, (0.20 g, 0.38 mmol) and potassium carbonate (0.26 g, 1.88 mmol) in tetrahydrofuran (5 mL) was added dropwise propionyl chloride (0.05 mL, 0.56 mmol). The reaction mixture was allowed to stir at room temperature overnight. The crude material was concentrated and purified via prep-TLC ($CH_2Cl_2$:2M $NH_3$ in MeOH, 97:3) to afford 0.09 g (42%) of the desired product as a white powder. MS m/z 589.1 $(M+H)^+$; Retention time (LC-MS): 3.68 min.

EXAMPLE 17

3-(3-tert-Butyl-5-{[(2-fluoro-4-{[2-(methylcarbamoyl)pyridin-4-yl]oxy}phenyl)carbamoyl]amino}-1H-pyrazol-1-yl)benzyl 3-methylbutanoate

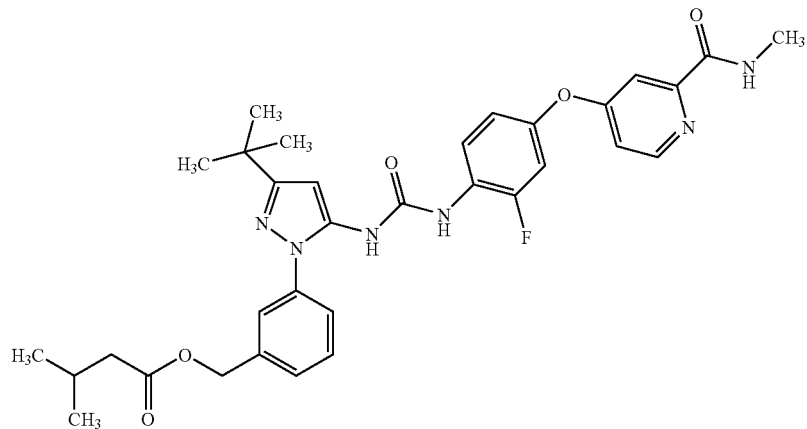

To a 0° C. solution of example 1, (4-{4-[({3-tert-butyl-1-[3-(hydroxymethyl)phenyl]-1H-pyrazol-5-yl}carbamoyl)amino]-3-fluorophenoxy}-N-methylpyridine-2-carboxamide, (0.10 g, 0.19 mmol) in dichloromethane (1.0 mL)/pyridine (0.3 mL) was added dropwise 3-methylbutanonyl chloride (0.02 mL, 0.23 mmol). The reaction mixture was allowed to warm to room temperature and stir for 72 h. The reaction mixture was diluted with EtOAc and washed with sat. aqueous $NaHCO_3$. The combined organic layer was washed with brine, dried and concentrated. The crude material was purified via column chromatography ($CH_2Cl_2$: MeOH, 100% $CH_2Cl_2$ to 98.5:1.5) to afford 0.02 g (18%) of the desired product as a white solid. MS m/z 617.3 $(M+H)^+$; Retention time (LC-MS): 3.89 min.

BIOLOGICAL EVALUATION

In order that this invention may be better understood, the following examples are set forth. These examples are for the purpose of illustration only, and are not to be construed as limiting the scope of the invention in any manner. All publications mentioned herein are incorporated by reference in their entirety.

Demonstration of the activity of the compounds of the present invention may be accomplished through in vitro, ex vivo, and in vivo assays that are well known in the art. For example, to demonstrate the activity of the compounds of the present invention, the following assays may be used.

Biological Assay Examples

Flk-1 (Murine VEGFR-2) Biochemical Assay

This assay was performed in 96-well opaque plates (Costar 3915) in the TR-FRET format. Reaction conditions were as follows: 10 μM ATP, 25 nM poly GT-biotin, 2 nM Eu-labelled phospho-Tyr Ab (PY20 Perkin Elmer), 10 nM APC (Perkin Elmer), 7 nM Flk-1 (kinase domain), 1% DMSO, 50 mM HEPES pH 7.5, 10 mM $MgCl_2$, 0.1 mM EDTA, 0.015% BRIJ, 0.1 mg/mL BSA, 0.1% mercapto-ethanol). Reaction was initiated upon addition of enzyme. Final reaction volume in each well was 100 μL. Plates were read at both 615 and 665 nM on a Perkin Elmer Victor V Multilabel counter at about 1.5-2.0 hours after reaction initiation. Signal was calculated as a ratio: (665 nm/615 nm)*10000 for each well.

c-Met Biochemical Assay

An ELISA format was used for the c-Met biochemical assay. This assay uses the C-terminal HIS-tagged intracellular kinase domain (956 to 1390 amino acids) human recombinant c-Met in 96-well plates. 96-Well plates (Costar #9018) coated with poly(GluTyr) (Sigma # P0275) were used in this assay. The poly(GluTyr) substrate coated on the plate was phosphorylated in a 100 μL reaction volume with 2 nM c-Met protein in an assay buffer (50 mM HEPES pH7.0, 5 mM $MnCl_2$, 0.1% BSA, 0.5 mM sodium orthovanadate, 0.1% β-mercaptoethanol), with 0.2 μM ATP (Sigma #A7699). 2 μL of compounds were added in as an 8-point $IC_{50}$ dose curve ranging from 10 uM to 128 pM at a final concentration of 1% DMSO. After 25 minutes of incubation, the assay reaction was stopped with 25 μL of 100 mM EDTA. The plates were then washed, and wells were treated with 100 μL of 80 ng/mL anti-4G10-HRP antibody (Upstate #16-105) for 1 h. Plates were washed one final time, and were developed with 100 μL 3,3',5,5'-TMB (Sigma #T8665), and quenched with 100 μL 1M HCl. Plates were read on a Victor 2 plate reader (Perkin Elmer) and $IC_{50}$ analysis and calculation were performed using in-house software.

Bcr-Abl Wild Type and Mutant T315I Biochemical Assay

Bcr-Abl-wt or mutant Bcr-Abl-T315I kinase (0.17 nM) was incubated with Myelin Basic Protein (MBP, 2 μM) in assay buffer consisting of 50 mM Tris pH 7.5, 10 mM $MgCl_2$, 1 mM EGTA, 2 mM DTT, 50 μM ATP and 0.4 μCi of $^{33}$P-ATP. Test compounds were added at varying concentrations (final DMSO conc=1%) prior to the addition of ATP. The reaction mixture was incubated for 1 hour at 32° C. The reaction was then stopped by addition of phosphoric acid (final conc=1%) and samples were transferred to filtermats and read in a beta-plate reader. Inhibition of MBP phosphorylation by Bcr-Abl-wt or Bcr-Abl-T315I was analyzed by using a 4 parameter fit and in-house software.

Example 1 showed IC$_{50}$<500 nM in biochemical assays for Flk-1, c-Met, wild type Bcr-Abl and mutant T315I Bcr-Abl. Examples 9, 10, 11, 14, 15, and 16 showed IC$_{50}$<1 μM in biochemical assays for Flk-1, c-Met, wild type Bcr-Abl and mutant T315I Bcr-Abl and examples 8, 12, and 17 showed IC$_{50}$<20 μM in biochemical assays for c-Met, and T315I Bcr-Abl.

In vitro Tumor Cell Proliferation Assay

The adherent tumor cell proliferation assay used to test the compounds of the present invention involves a readout called Cell Titre-Glo developed by Promega (Cunningham, BA "A Growing Issue: Cell Proliferation Assays. Modern kits ease quantification of cell growth" *The Scientist* 2001, 15 (13), 26; and Crouch, S P et al., "The use of ATP bioluminescence as a measure of cell proliferation and cytotoxicity" *Journal of Immunological Methods* 1993, 160, 81-88).

H460 cells (lung carcinoma, purchased from ATCC) were plated in 96-well plates at 3000 cells/well in complete media with 10% Fetal Calf Serum and incubated 24 hours at 37° C. Twenty-four hours after plating, test compounds were added over a final concentration range of 10 nM to 20 μM in serial dilutions at a final DMSO concentration of 0.2%. Cells were incubated for 72 hours at 37° C. in complete growth media after addition of the test compound. On day 4, using a Promega Cell Titer Glo Luminescent® assay kit, the cells were lysed and 100 microliters of substrate/buffer mixture was added to each well, mixed and incubated at room temperature for 8 minutes. The samples were read on a luminometer to measure the amount of ATP present in the cell lysates from each well, which corresponds to the number of viable cells in that well. Values read at 24-hour incubation were subtracted as Day 0. For determination of IC$_{50}$ values, a linear regression analysis was used to determine drug concentration which results in a 50% inhibition of cell proliferation using this assay format. This protocol was applied to different cell lines of interest, which include, but are not limited to, CAKI-1, MKN45, HCC2998, K562, H441, K812, MEG01, SUP15, HCT116, BaF3-Abl(wt) and BaF3-Abl(T315I).

Example 1 and derivatives thereof (Examples 9, 11, 12, 13, and 14 showed antiproliferative properties (IC$_{50}$<5 μM) in one or more cell lines of interest. Cell lines of interest include, but are not limited to, CAKI-1, MKN45, HCC2998, K562, H441, K812, MEG01, SUP15, HCT116, BaF3-Abl(wt) and BaF3-Abl(T315I).

Table 1 illustrates the results of cell proliferation assays for various BaF3 cell lines (which express different forms of Bcr-Abl, including the wild type form), and K562 (a human cell line expressing wild type Bcr-Abl). It is of particular interest that BaF3-Abl(T315I), BaF3-Abl(E255K), BaF3-Abl(M351T), and BaF3-Abl(Y253F) are cell types that express Imatinib-resistant mutations of Bcr-Abl that have been observed in patients. Data for Example 1 are provided. For the BaF3 parental cell line that does not express Bcr-Abl, cell proliferation IC$_{50}$ values greater than 3 μM were determined for Example 1.

Table 1. Cell proliferation IC$_{50}$ values (M) for various cell lines expressing wild-type and mutant forms of Bcr-Abl treated with Example 1.

TABLE 1

| Cell type | Cell proliferation IC$_{50}$ (M) |
|---|---|
| K562 | 1.58E−09 |
| BaF3-Abl(wt) | 3.84E−09 |
| BaF3-Abl(T315I) | 3.41E−08 |
| BaF3-Abl(E255K) | 5.03E−08 |
| BaF3-Abl(M351T) | 8.11E−09 |
| BaF3-Abl(Y253F) | 5.64E−09 |

Examples 9, 11, 12, 13 and 14 showed IC$_{50}$<10 μM in the BaF3-Abl(M351T) proliferation assay.

It is believed that one skilled in the art, using the preceding information and information available in the art, can utilize the present invention to its fullest extent. It should be apparent to one of ordinary skill in the art that changes and modifications can be made to this invention without departing from the spirit or scope of the invention as it is set forth herein. The topic headings set forth above and below are meant as guidance where certain information can be found in the application, but are not intended to be the only source in the application where information on such topic can be found. All publications and patents cited above are incorporated herein by reference.

What is claimed is:

1. A compound having the formula:

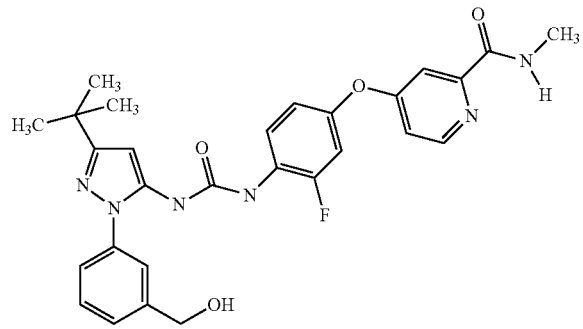

which is 4-{4-[({3-tert-Butyl-1-[3-(hydroxymethyl)phenyl]-1H-pyrazol-5-yl}-carbamoyl)amino]-3-fluorophenoxy}-N-methylpyridine-2-carboxamide, or a pharmaceutically acceptable salt thereof or an ester prodrug thereof.

2. A compound of claim 1 wherein the prodrug is selected from the group consisting of:

a) 3-(3-tert-Butyl-5-{[(2-fluoro-4-{[(2-(methylcarbamoyl)pyridin-4-yl]oxy}phenyl)carbamoyl]amino}-1 H-pyrazol-1-yl)benzyl-N-[(9H-fluoren-9-ylmethoxy) carbonyl]D valinate of the formula:

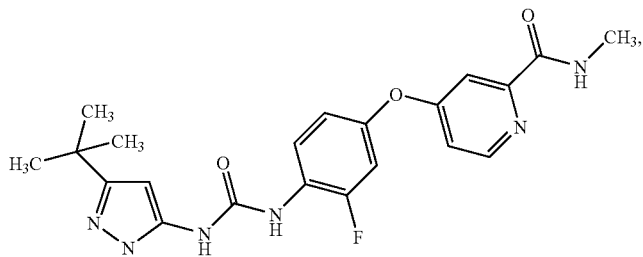
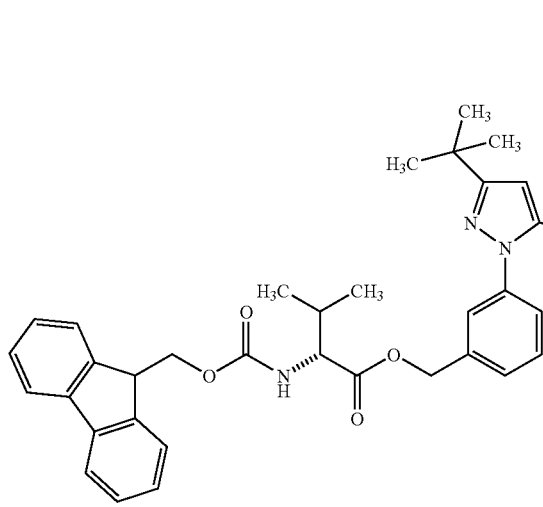
b) 3-(3-tert-Butyl-5-{[(2-fluoro-4-{[(2-(methylcarbamoyl)pyridin-4-yl]oxy}phenyl)-carbamoyl]amino}-1H-pyrazol-1-yl)benzyl D-valinate of the formula:
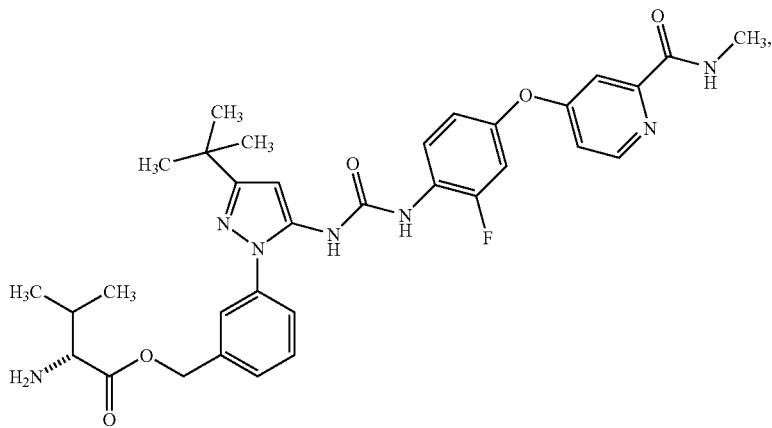
c) 3-(3-tert-Butyl-5-{[(2-fluoro-4-{[2-(methylcarbamoyl)pyridin-4-yl]oxy}-phenyl)carbamoyl]amino}-1H-pyrazol-1-yl)benzyl L-valinate of the formula:
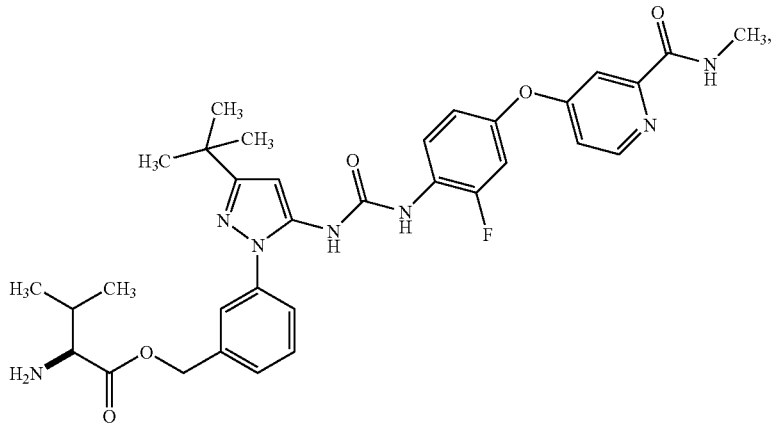

d) 3-(3-tert-Butyl-5-{[(2-fluoro-4-{[2-(methylcarbamoyl)pyridin-4-yl]oxy}-phenyl)carbamoyl]amino}-1H-pyrazol-1-yl)benzyl acetate of the formula:

e) di-tert-butyl 3-(3-tert-butyl-5-{[(2-fluoro-4-{[2-(methylcarbamoyl)pyridin-4-yl]oxy}phenyl)carbamoyl]amino}-1H-pyrazol-1-yl)benzyl phosphate of the formula:

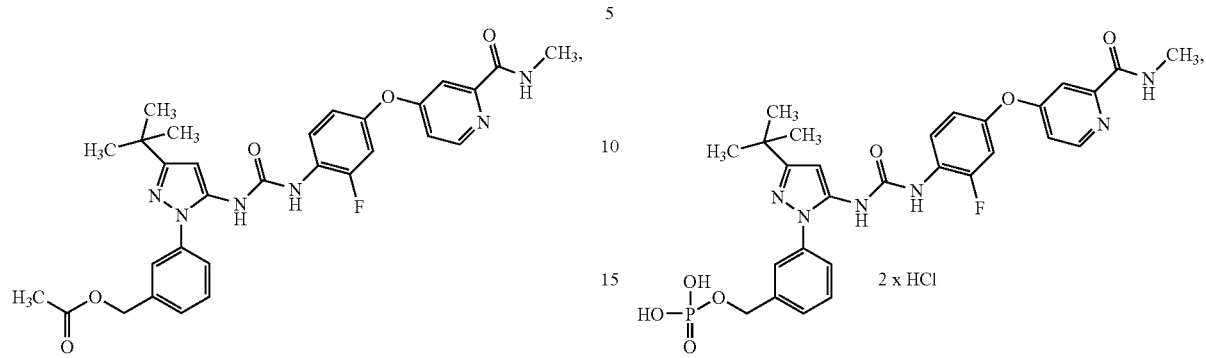

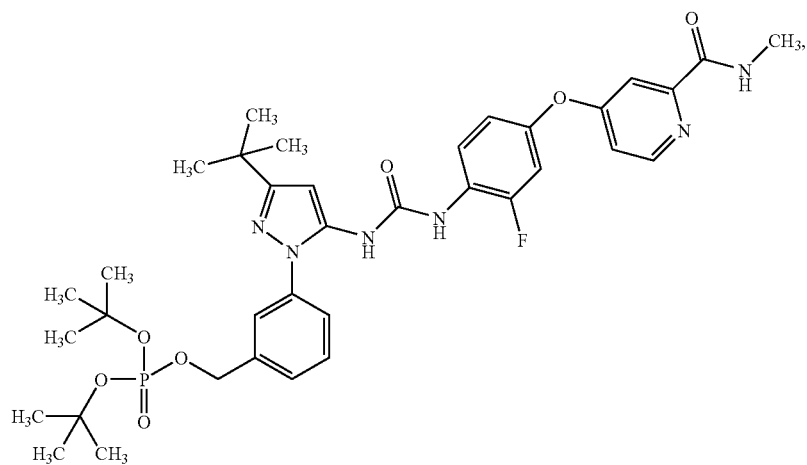

f) 3-(3-tert-Butyl-5-{[(2-fluoro-4-{[2-(methylcarbamoyl)pyridin-4-yl]oxy}-phenyl)carbamoyl]amino}-1H-pyrazol-1-yl)benzyl dihydrogen phosphate dihydrochloride of the formula:

g) 4-{[3-tert-Butyl-5-{[(2-fluoro-4-{[2-(methylcarbamoyl)pyridin-4-yl]oxy}-phenyl)carbamoyl]amino}-1H-pyrazol-1-yl)benzyl]oxy}-4-oxobutanoic acid of the formula:

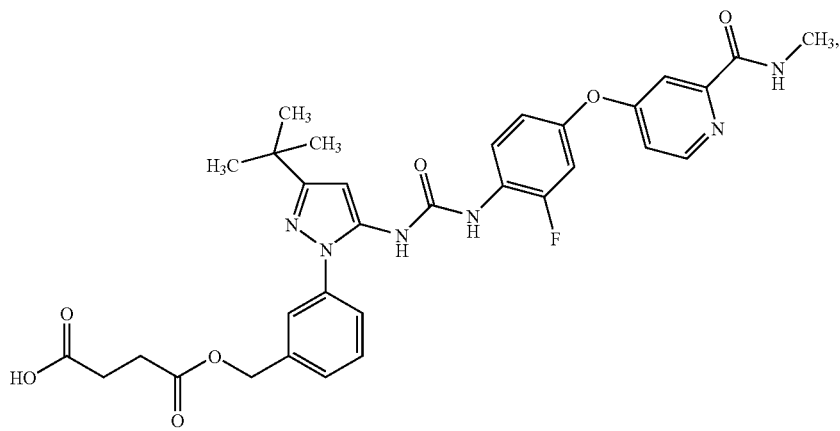

h) 3-(3-tert-Butyl-5-{[(2-fluoro-4-{2-(methylcarbamoyl)pyridin-4-yl]oxy}phenyl)carbamoyl]amino}-1H-pyrazol-1-yl)benzyl methoxyacetate of the formula:

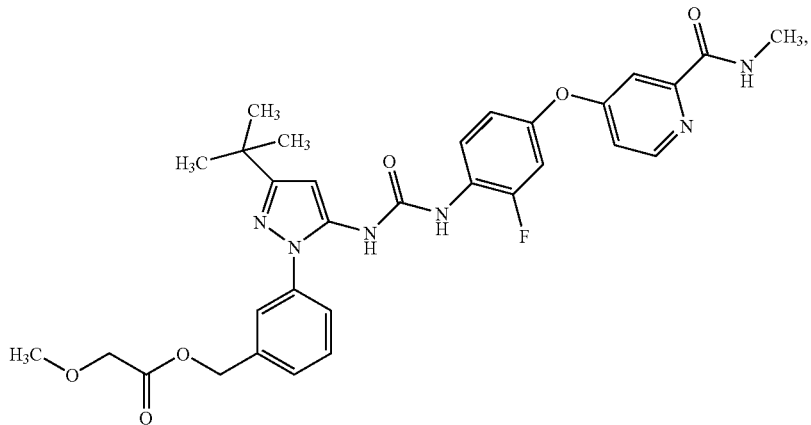

i) 3-(3-tert-butyl-5-{[(2-fluoro-4{[2-(methylcarbamoyl)pyridin-4-yl]oxy}phenyl)carbamoyl]amino}-1H-pyrazol-1-yl)benzyl propionate of the formula:

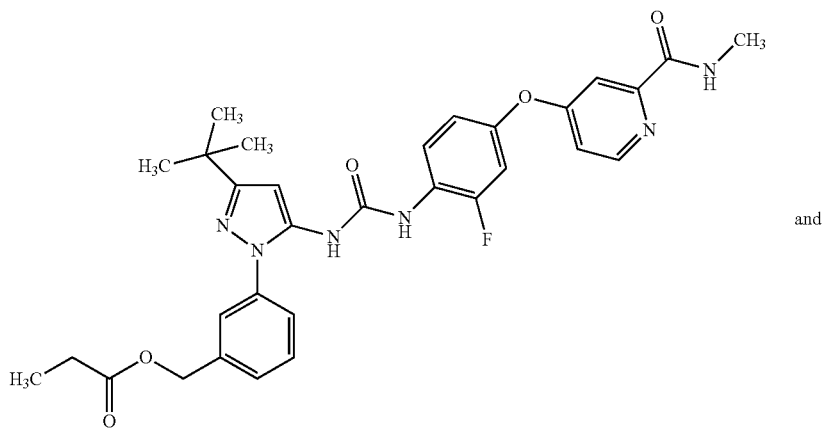

and j) 3-(3-tert-Butyl-5-{[(2-fluoro-4-{[2-(methylcarbamoyl)pyridin-4-yl]oxy}phenyl)carbamoyl]amino }-1H-pyrazol-1-yl)benzyl 3-methylbutanoate of the formula:

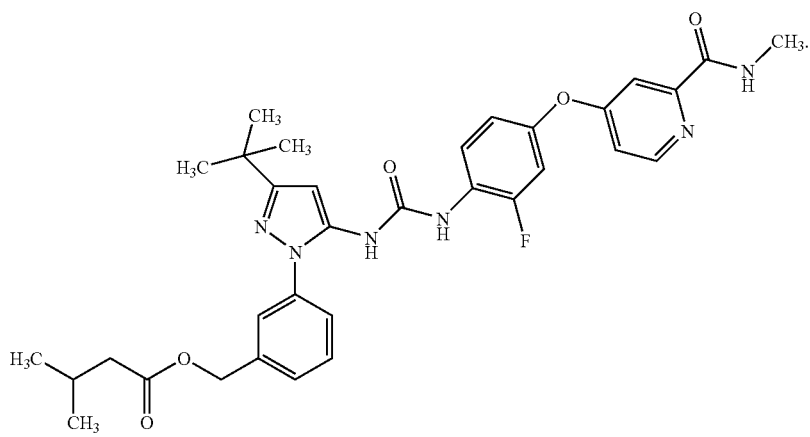

3. A compound of claim 1 wherein the salt is selected from the group consisting of
   a) 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide, bis(4-methylbenzenesulfonate)salt,
   b) 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide, dimethanesulfonate salt,
   c) 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide, dihydrochloride salt,
   d) 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide, bis(benzenesulfonate) salt,
   e) 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide, dihydrogen bromide salt and
   f) 4-{4-[({3-tert-Butyl-1-[3-(hydroxymethyl)phenyl]-1H-pyrazol-5-yl}carbamoyl)amino]-3-fluorophenoxy}-N-methylpyridine-2-carboxamide, hydrogen sulfate salt.

4. A pharmaceutical composition comprising:
a compound having the formula:

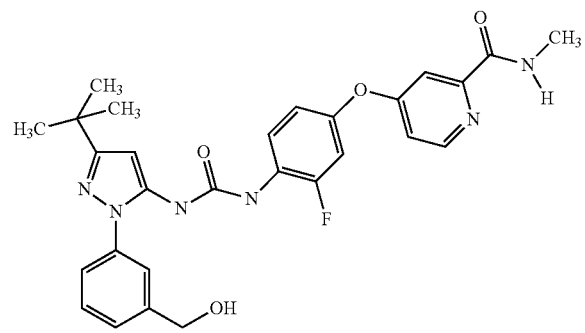

which is 4-{4-[({3-tert-Butyl-1-[3-(hydroxymethyl)phenyl]-1H-pyrazol-5-yl}-carbamoyl)amino]-3-fluorophenoxy}-N-methylpyridine-2-carboxamide, or a pharmaceutically acceptable salt thereof, or an ester prodrug thereof.

5. A pharmaceutical composition comprising a compound of claim 2 and a physiologically acceptable carrier.

6. A pharmaceutical composition comprising a compound of claim 3 and a physiologically acceptable carrier.

7. A method of treating hyper-proliferative disorders comprising administering to a mammal in need thereof a therapeutically effective amount of a compound of claim 1.

8. A method of treating hyper-proliferative disorders comprising administering to a mammal in need thereof a therapeutically effective amount of a composition of claim 4.

9. A method according to claim 8, wherein said hyper-proliferative disorder is cancer.

10. A method according to claim 9, wherein said cancer is of the breast, respiratory tract, brain, reproductive organs, digestive tract, urinary tract, eye, liver, skin, head and/or neck, thyroid, parathyroid and/or their distant metastases.

11. A method according to claim 9, wherein said cancer is lymphoma, sarcoma, or leukemia.

12. A method according to claim 10, wherein said breast cancer is invasive ductal carcinoma, invasive lobular carcinoma, ductal carcinoma in situ, or lobular carcinoma in situ;
   said respiratory tract cancer is small-cell lung carcinoma, non-small-cell lung carcinoma, bronchial adenoma or pleuropulmonary blastoma;
   said brain cancer is a tumor of the brain stem, hypophtalmic glioma, cerebellar astrocytoma, cerebral astrocytoma, medulloblastoma, ependymoma, neuroectodermal or pineal tumor;
   said tumor of the male reproductive organ is a prostate or testicular cancer;
   said cancer of the female reproductive organ is endometrial, cervical, ovarian, vaginal, vulvar, or sarcoma of the uterus;
   said cancer of the digestive tract is anal, colon, colorectal, esophageal, gallbladder, gastric, pancreatic, rectal, small-intestine or salivary gland;
   said cancer of the urinary tract is bladder, penile, kidney, renal pelvis, ureter or urethral;
   said eye cancer is intraocular melanoma or retinoblastoma;
   said liver cancer is hepatocellular carcinoma, liver cell carcinomas with or without fibrolamellar variant, cholangiocarcinoma or mixed hepatocellular cholangiocarcinoma;
   said skin cancer is squamous cell carcinoma, Kaposi's sarcoma, malignant melanoma, Merkel cell skin cancer or non-melanoma skin cancer;
   said head-and-neck cancer is laryngeal, hypopharyngeal, nasopharyngeal, oropharyngeal, lip or oral cavity cancer;
   said lymphoma is AIDS-related lymphoma, non-Hodgkin's lymphoma, cutaneous T-cell lymphoma, Hodgkin's disease or lymphoma of the central nervous system;
   said sarcomas is a sarcoma of the soft tissue, osteosarcoma, malignant fibrous histiocytoma, lymphosarcoma or rhabdomyosarcoma;
   said leukemia is acute myeloid leukemia, acute lymphoblastic leukemia, chronic lymphocytic leukemia, chronic myelogenous leukemia or hairy cell leukemia 13. A method of treating angiogenesis disorders comprising administering to a mammal in need thereof a therapeutically effective amount of a compound of claim 1.

14. A composition of claim 4, further including an anti-hyper-proliferative agent.

15. A composition of claim 14, wherein said anti-hyperproliferative agent is epothiline or its derivative, irinotecan, raloxifen or topotecan.

16. A composition of claim 4, wherein said additional pharmaceutical agent is
   aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DAUNOXOME® (daunorubicin), decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, EPOGEN® (epotin-alpha), eptaplatin, ergamisol, estrace, estradiol, estramustine phosphate sodium, ethinyl estradiol, ethyol, etidronic acid, etopophos, etoposide, fadrozole, FARESTON® (Toremitene), filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, GLEEVEC® (imatinib mesylate), GLIADEL® (wafer), goserelin, granisetron HC1, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, INTRON-A (interferon alfa-2b, recombinant) iressa, irinotecan, kytril, lentinan sulphate, letrozole, leucovorin, leuprolide, leuprolide acetate, levamisole, levofolinic acid calcium salt, levothroid, LEVOXYL ® (levothyroxine sodium tablets,), lomustine, lonidamine, marinol, mechlorethamine, mecobalamin, medroxyprogesterone acetate, megestrol acetate, melphalan, MENEST® (esterified estrogens), 6 -mercaptopurine, Mesna, methotrexate, metvix, miltefosine, minocycline, mitomycin C, mitotane, mitoxantrone, MODRENAL® (trilostane), MYOCET ® (non-pegylated liposomal doxorubicin), nedaplatin, neulasta, neumega, neupogen, nilutamide, NOLVADEX® (tamoxifen citrate), NSC-631570, OCT-43, octreotide, ondansetron HC1, oraprad, oxaliplatin, paclitaxel, pediapred, pegaspargase, PEAGASYS (peginterferon alfa-2a), pentostatin, picibanil, pilocarpine HC1, pirarubicin, plicamycin, porfimer sodium, prednimustine, prednisolone, prednisone, PREMARIN® (conjugated estrogen tablets), procarbazine, procrit, raltitrexed, rebif, rhenium-186 etidronate, rituximab, roferon-A, romurtide, salagen, sandostatin, sargramostim, semustine, sizofiran, sobuzoxane, solu-medrol, sparfosic acid, stem-cell therapy, streptozocin, strontium-89 chloride, synthroid, tamoxifen, tamsulosin, tasonermin, tastolactone, TAXOTERE® (docetaxel), teceleukin, temozolomide, teniposide, testosterone propionate, TESTRED® (Methyltestosterone), thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, ZOFRAN® (ondansetron), ABI-007, acolbifene, actimmune, affinitak, aminopterin, arzoxifene, asoprisnil, atamestane, atrasentan, BAY 43-9006 (sorafenib), avastin, CCI-779, CDC-501, CELEBREX® (anti-inflamatory), cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis -retinoic acid, satraplatin, seocalcitol, T-138067, TARCEVA® (erlotinib), taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

* * * * *